United States Patent
Schmidt et al.

(10) Patent No.: US 7,315,667 B2
(45) Date of Patent: Jan. 1, 2008

(54) PROPAGATING LIGHT TO BE SENSED

(75) Inventors: Oliver Schmidt, Palo Alto, CA (US);
Peter Kiesel, Palo Alto, CA (US);
Patrick Y. Maeda, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 104 days.

(21) Appl. No.: 11/315,387

(22) Filed: Dec. 22, 2005

(65) Prior Publication Data

US 2007/0146888 A1  Jun. 28, 2007

(51) Int. Cl.
*G02B 6/00* (2006.01)
*G02B 5/28* (2006.01)
*G02B 6/32* (2006.01)
*G01J 1/04* (2006.01)

(52) U.S. Cl. .................... 385/12; 385/31; 385/38; 385/33; 385/34; 385/88; 385/92; 385/93; 385/122; 250/227.11; 250/227.14; 250/227.18; 359/589; 359/362; 359/433; 359/577; 359/580; 359/586

(58) Field of Classification Search .................. 385/12, 385/31, 33, 34, 35, 38, 49, 88, 89, 92, 93, 385/94, 122; 250/227.11, 227.14, 227.18; 359/589, 362, 433, 577, 580, 586
See application file for complete search history.

(56) References Cited

U.S. PATENT DOCUMENTS 2,708,389 A   5/1955   Kavanagh ............... 350/166
3,973,118 A   8/1976   LaMontagne ............ 250/226
4,081,277 A   3/1978   Brault et al. ............. 96/38.2

(Continued)

FOREIGN PATENT DOCUMENTS

EP   1324 018 A2   7/2003   .............. 385/12 X (Continued)

OTHER PUBLICATIONS

Othonos, A., and Kalli, K., "Fiber-Bragg Gratings—Fundamentals and Applications in Telecommunications and Sensing", Artech House, Norwood, MA, 1999, pp. 304-330.

(Continued)

*Primary Examiner*—Brian M. Healy
(74) *Attorney, Agent, or Firm*—Leading-Edge Law Group, PLC; James T. Beran

(57) ABSTRACT

Light to be sensed is spreaded across an entry surface of a transmission structure with a laterally varying energy transmission function. For example, the light could be output from a stimulus-wavelength converter, provided through an optical fiber, or it could come from a point-like source or broad area source. Output photons from the transmission structure can be photosensed by photosensing components such as an array, position sensor, or array of position sensors. Wavelength information from the light can be obtained in response to the photosensing component. Spreading can be performed by air, gas, transparent material, or vacuum in a gap, by a region or other part of a lens, or by an optical fiber end surface. If the light comes from more than one source, a propagation component can both spread the light and also keep light from the sources separate.

32 Claims, 22 Drawing Sheets

U.S. PATENT DOCUMENTS

| | | | |
|---|---|---|---|
| 4,764,670 A | 8/1988 | Pace et al. | 250/226 |
| 4,957,371 A | 9/1990 | Pellicori et al. | 356/419 |
| 4,976,542 A | 12/1990 | Smith | 356/346 |
| 5,080,462 A * | 1/1992 | Goto | 385/122 |
| 5,144,498 A | 9/1992 | Vincent | 359/885 |
| 5,166,755 A | 11/1992 | Gat | 356/419 |
| 5,305,082 A | 4/1994 | Bret | 356/419 |
| 5,324,401 A | 6/1994 | Yeung et al. | 204/180.1 |
| 5,777,329 A | 7/1998 | Westphal et al. | 250/339.02 |
| 5,784,507 A | 7/1998 | Holm-Kennedy et al. | 385/31 |
| 5,792,663 A | 8/1998 | Fry et al. | 436/73 |
| 5,801,831 A | 9/1998 | Sargoytchev | 356/346 |
| 5,825,792 A | 10/1998 | Villeneuve et al. | 372/32 |
| 5,864,641 A | 1/1999 | Murphy et al. | 385/12 |
| 5,945,676 A | 8/1999 | Khalil et al. | 250/339.12 |
| 5,953,138 A * | 9/1999 | Ellis | 398/75 |
| 6,040,578 A | 3/2000 | Malin et al. | 250/339.12 |
| 6,108,463 A | 8/2000 | Herron et al. | 385/12 |
| 6,137,117 A | 10/2000 | Feldstein et al. | 250/573 |
| 6,192,168 B1 | 2/2001 | Feldstein et al. | 385/12 |
| 6,249,346 B1 | 6/2001 | Chen et al. | 356/328 |
| 6,275,628 B1 | 8/2001 | Jones et al. | 385/29 |
| 6,295,130 B1 | 9/2001 | Sun et al. | 356/454 |
| 6,307,623 B1 * | 10/2001 | Papuchon et al. | 356/152.1 |
| 6,353,475 B1 | 3/2002 | Jensen et al. | 356/244 |
| 6,399,405 B1 | 6/2002 | Chen et al. | 438/22 |
| 6,405,073 B1 | 6/2002 | Crowley et al. | 600/476 |
| 6,429,022 B1 | 8/2002 | Kunz et al. | 436/164 |
| 6,459,080 B1 | 10/2002 | Yin et al. | 250/288 |
| 6,483,959 B1 | 11/2002 | Singh et al. | 385/12 |
| 6,505,775 B1 | 1/2003 | Gu et al. | 235/454 |
| 6,519,037 B2 | 2/2003 | Jung et al. | 356/419 |
| 6,525,308 B1 | 2/2003 | Schmidt-Hattenberger | 250/227.23 |
| 6,558,945 B1 | 5/2003 | Kao | 435/287.2 |
| 6,577,780 B2 | 6/2003 | Lockhart | 385/12 |
| 6,580,507 B2 | 6/2003 | Fry et al. | 356/436 |
| 6,603,548 B2 | 8/2003 | Church et al. | 356/326 |
| 6,608,679 B1 | 8/2003 | Chen et al. | 356/328 |
| 6,630,999 B2 | 10/2003 | Shroder | 356/419 |
| 6,639,679 B2 | 10/2003 | Frojdh | 356/454 |
| 6,665,113 B2 * | 12/2003 | Aso et al. | 359/326 |
| 6,781,690 B2 | 8/2004 | Armstrong et al. | 356/301 |
| 6,785,002 B2 | 8/2004 | Zarrabian et al. | 356/454 |
| 6,796,710 B2 * | 9/2004 | Yates et al. | 374/161 |
| 6,800,849 B2 | 10/2004 | Staats | 250/288 |
| 6,867,420 B2 | 3/2005 | Mathies et al. | 250/458.1 |
| 6,870,149 B2 | 3/2005 | Berezin | 250/208.1 |
| 6,887,713 B2 | 5/2005 | Nelson et al. | 436/173 |
| 7,106,441 B2 | 9/2006 | Sun et al. | 356/328 |
| 7,248,361 B2 | 7/2007 | Kiesel et al. | 356/318 |
| 7,268,868 B2 * | 9/2007 | Kiesel et al. | 356/301 |
| 7,291,824 B2 | 11/2007 | Kiesel et al. | 250/208.1 |
| 2002/0155485 A1 | 10/2002 | Kao | 435/6 |
| 2003/0000835 A1 | 1/2003 | Witt et al. | 204/451 |
| 2003/0077660 A1 | 4/2003 | Pien et al. | 435/7.1 |
| 2003/0161024 A1 | 8/2003 | Zhang et al. | 359/260 |
| 2003/0235924 A1 | 12/2003 | Adams et al. | 436/172 |
| 2004/0031684 A1 | 2/2004 | Witt | 204/452 |
| 2004/0032584 A1 | 2/2004 | Honda et al. | 356/328 |
| 2004/0038386 A1 | 2/2004 | Zesch et al. | 356/319 X |
| 2004/0132214 A1 | 7/2004 | Lin et al. | 436/518 |
| 2004/0141884 A1 | 7/2004 | Unno et al. | 422/100 |
| 2004/0145738 A1 | 7/2004 | Sun et al. | 356/328 |
| 2004/0223881 A1 | 11/2004 | Cunningham et al. | 422/82.05 |
| 2004/0228375 A1 | 11/2004 | Ghosh et al. | 372/32 |
| 2005/0042615 A1 | 2/2005 | Smith et al. | 735/6 |
| 2005/0068526 A1 | 3/2005 | Avrutsky | 356/328 |
| 2005/0084203 A1 | 4/2005 | Kane | 385/16 |
| 2005/0128479 A1 | 6/2005 | Gilbert et al. | 356/338 |
| 2005/0162650 A1 | 7/2005 | Yamamoto | 356/328 |
| 2006/0039009 A1 | 2/2006 | Kiesel et al. | 356/519 |
| 2006/0046312 A1 | 3/2006 | Kiesel et al. | 436/518 |
| 2006/0092413 A1 | 5/2006 | Kiesel et al. | 356/301 |
| 2006/0121555 A1 | 6/2006 | Lean et al. | 435/30 |
| 2006/0193550 A1 | 8/2006 | Wawro et al. | 385/12 |
| 2006/0274313 A1 | 12/2006 | Gilbert et al. | 356/432 |
| 2007/0009380 A1 | 1/2007 | Cunningham | 422/58 |
| 2007/0076210 A1 * | 4/2007 | Kiesel et al. | 356/454 |
| 2007/0145236 A1 | 6/2007 | Kiesel et al. | 250/208.1 |
| 2007/0145249 A1 | 6/2007 | Kiesel et al. | 250/221 |
| 2007/0146704 A1 | 6/2007 | Schmidt et al. | 356/338 |
| 2007/0147189 A1 | 6/2007 | Schmidt et al. | 369/13.47 |
| 2007/0147726 A1 | 6/2007 | Kiesel et al. | 385/12 |
| 2007/0147728 A1 | 6/2007 | Schmidt et al. | 385/14 |
| 2007/0148760 A1 | 6/2007 | Kiesel et al. | 435/287.2 |

FOREIGN PATENT DOCUMENTS

| | | | |
|---|---|---|---|
| EP | 1801553 A1 | 6/2007 | 385/12 X |
| WO | WO95/20144 | 7/1995 | 385/147 X |

OTHER PUBLICATIONS

Fuhr, P.L., "Measuring with Light", Sensors Magazine Online, May 2000, 11 pages.

Udd, E., "Good Sense", spie's oemagazine, Aug. 2002, pp. 27-29.

Johnson, S.G., and Joannopoulos, J.D., "Introduction to Photonic Crystals: Bloch's Theorem, Band Diagrams. and Gaps (But No Defects)". Feb. 3, 2003, pp. 1-16, and attched 49 pages of slides.

Wippich, M., and Dessau, K.L., "Tunable Lasers and Fiber-Bragg-Grating Sensors", The Industrial Physicist, Jun./Jul. 2003, pp. 24-27.

Prasad, P.N., "Introduction to Biophotonics", John Wiley & Sons, Hoboken, N.J., 2003, pp. 311-356.

Sivaprakasam, V., Huston, A., Eversole, J., and Scotto, C., "Multiple UV Wavelength Excitation and Fluorescence of Bioaerosols", 2nd Joint Conference on Point Detection, Williamsburg, VA, 2004, 10 pages.

Fuji-Keizai USA, "Biosensor Market, R&D and Commerical Implication", printed from www.fuji-keizai.com/e/report/biosensor2004_e.html on Dec. 21, 2005, 5 pages.

SRU Biosystems, Inc., "BIND Biosensor TM Technology", Apr. 3, 2004 excerpt, printed from www.srubiosystems.com/tech/index.html on Dec. 8, 2005, 1 page.

Spear, J. D., and Russo, R.E., "Low noise position sensitive detector for optical probe beam deflection measurements", Rev. Sci. Instrum., vol. 67, No. 7, Jul. 1996, pp. 2481-2484.

Johnson, S.G., "Photonic Crystals: Periodic Surprises in Electromagnetism", printed from ab-initio.mit.edu on Oct. 5, 2006, 3 pages.

Sailor, M.J., "Nanostructured Sensors—'Smart Dust'", printed from www-chem.ucsd.edu on Oct. 5, 2006, 2 pages.

Agilant Technologies, "Agilent 83453B High-Resolution Spectrometer—Technical Specifications", Feb. 2005, pp. 1-8.

Liu, G.L., and Lee, L.P., "Nanowell surface enhanced Raman scattering arrays fabricated by soft-lithography for label-free biomolecular detections in integrated microfluidics", Applied Physics Letters, vol. 87, 2005, pp. 1-3.

Cunningham, B.T., Li, P., Schulz, S., Lin, B., Baird, C., Gerstenmaier, J., Genick, C., Wang, F., Fine, E., and Laing, L., "Label-Free Assays on the BIND System", Journal of Biomolecular Screening, vol. 9, No. 6, 2004, pp. 481-490.

Vollmer, F., Arnold, S., Braun, D., Teraoka, I., and Libchaber, A., "Multiplexed DNA Quantification by Spectroscopic Shift of Two Microsphere Cavities", Biophysical Journal, vol. 85, Sep. 2003, pp. 1-6.

Shah, M.A., Shanmugan, V., Chowdhury, G.K., and Akkipeddi, R., "Optomechanical design of tunable inP-based Fabry-Perot filters for wavelength division multiplexing applications", J. Microlith., Microfab., Microsyst., vol. 4(4), Oct.-Dec. 2005, pp. 041303-1 through 041303-8.

Schaefer, P., Williams, R.D., Davis, G.K., and Ross, R.A., "Accuracy of Position Detection Using a Position-Sensitive Detector". IEEE Transactions on Instrumentation and Measurement, vol. 47, No. 4, Aug. 1998, pp. 914-919.

Henry, J., and Livingstone, J., "Wavelength response of thin-film optical position-sensitive detectors", J. Opt. A: Pure Appl. Opt., vol. 4, 2002, pp. 527-534.

Adams, M.L., Enzelberger, M., Quake, S., and Scherer, A., "Microfluidic integration on detector arrays for absorption and fluorescence micro-spectrometers, "Sensors and Actuators A, vol. 104, 2003, pp. 25-31.

European Search Report and Annex for Counterpart EPO Application No. EP 06 12 6527, dated Apr. 5, 2007, 2 pages.

Communication from European Patent Office, including extended European search report with European Search Report and Annex and European search opinion for counterpart EPO Application No. EPO 6126527, dated Apr. 16, 2007, 6 pages.

Office communication in U.S. Appl. No. 10/922,870, mailed Jul. 26, 2007, 11 pages.

Amendment in U.S. Appl. No. 10/922,870, dated Apr. 30, 2007, 15 pages.

Amendment in U.S. Appl. No. 10/922,870, dates Sep. 14, 2007, 9 pages.

Office communication in U.S. Appl. No. 11/316,303, dated Aug. 31, 2007, 19 pages.

Amendment with Information Disclosure in U.S. Appl. No. 11/316,303, dated Apr. 26, 2007, 18 pages.

Notice of Allowance and Fee(s) Due and attached papers for U.S. Appl. No. 11/316,438, mailed Jul. 6, 2007, 20 pages.

Communication from European Patent Office, including extended European search report with European Search Report and Annex and European search opinion for counterpart EPO Application No. EPO 6126527, dated Apr. 16, 2007, 6 pages.

Office communication in U.S. Appl. No. 10/922,870, mailed Sep. 24, 2007, 3 pages, published in PAIR.

Second Amendment After Final Rejection in U.S. Appl. No. 10/922,870, dated Oct. 4, 2007, 9 pages, published in PAIR.

Notice of Allowance and Fee(s) Due in U.S. Appl. No. 10/922,870, dated Oct. 22, 2007, 7 pages, published in PAIR.

Office communication in U.S. Appl. No. 11/316,241, mailed Oct. 23, 2007, 28 pages, published in PAIR.

Office communication in U.S. Appl. No. 11/316,303, mailed Oct. 22, 2007, 3 pages, published in PAIR.

Amendment After Final Rejection in U.S. Appl. No. 11/316,303, dated Oct. 4, 2007, 14 pages, published in PAIR.

Notice of Allowance and Fee(s) Due and attached papers for U.S. Appl. No. 11/315,992, mailed Oct. 3, 2007, 19 pages, published in PAIR.

Office communication in U.S. Appl. No. 10/922,870, mailed Jul. 26, 2007, 11 pages, published in PAIR.

Amendment in U.S. Appl. No. 10/922,870, dated Apr. 30, 2007, 15 pages, published in PAIR.

Amendment in U.S. Appl. No. 10/922,870, dated Sep. 14, 2007, 9 pages, published in PAIR.

Office communication in U.S. Appl. No. 11/316,303, dated Aug. 31, 2007, 19 pages, published in PAIR.

Amendment with Information Disclosure in U.S. Appl. No. 11/316,303, dated Apr. 26, 2007, 18 pages, publsihed in PAIR.

Notice of Allowance and Fee(s) Due and attached papers for U.S. Appl. No. 11/316,438, mailed Jul. 6, 2007, 20 page, published in PAIR.

Communications from European Patent Office, including extended European search report with European Search Report and Annex and European search opinion for counterpart EPO Application No. EPO 6126527, dated Apr. 16, 2007, 6 pages.

* cited by examiner

FIG. 37
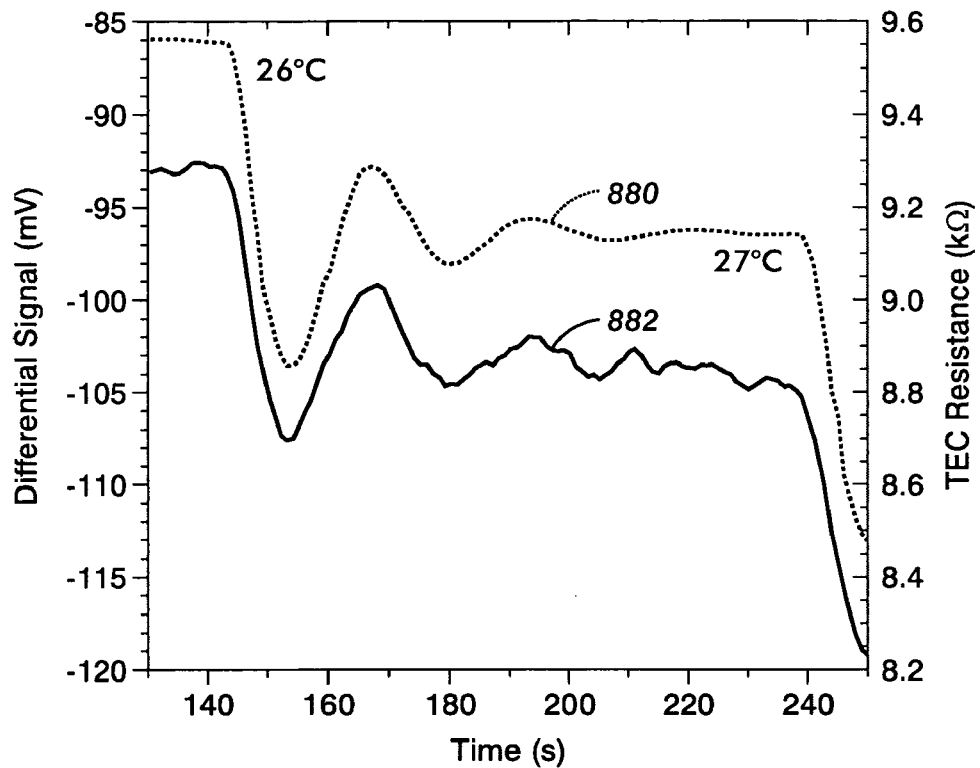
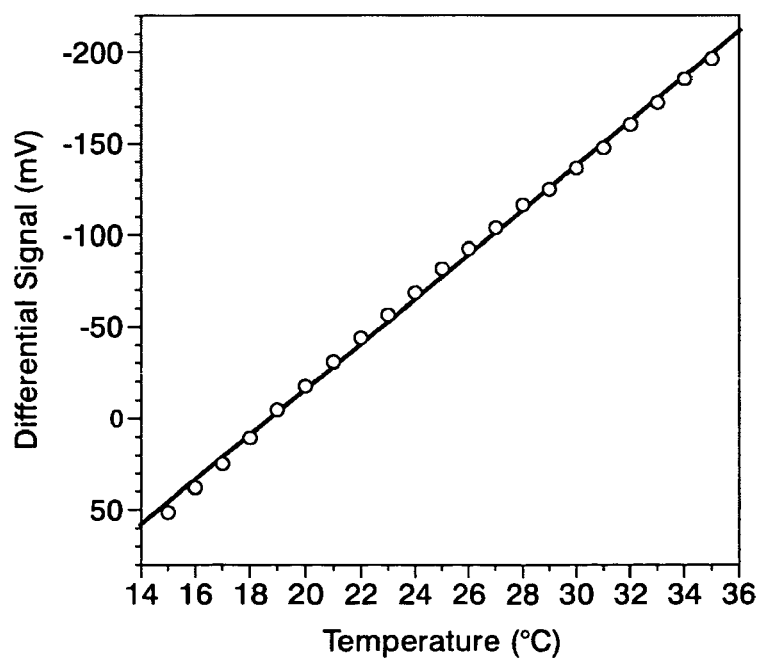
FIG. 38

PROPAGATING LIGHT TO BE SENSED

The present application is related to the following co-pending applications, each of which is hereby incorporated by reference in its entirety: "Chip-Size Wavelength Detector", U.S. patent application Ser. No. 10/922,870 pending; "Biosensor Using Microdisk Laser", U. S. patent application Ser. No. 10/930,758 pending; "Anti-resonant Waveguide Sensors", U.S. patent application Ser. No. 10/976,434 pending; "Photosensing Throughout Energy Range and in Subranges", U.S. patent application Ser. No. 11/316,438, pending; "Sensing Photon Energies of Optical Signals", U.S. patent application Ser. No. 11/315,926, pending; "Sensing Photon Energies Emanating From Channels or Moving Objects", U.S. patent application Ser. No. 11/315,386, pending; "Providing Light To Channels Or Portions", U.S. patent application Ser. No. 11/316,660, pending; "Sensing Photon Energies Emanating from Channels", U.S. patent application Ser. No. 11/315,992, pending; "Transmitting Light With Photon Energy Information", U.S. patent application Ser. No. 11/316,241, pending; and "Obtaining Analyte Information", U.S. patent application Ser. No. 11/316,303, pending.

BACKGROUND OF THE INVENTION

The present invention relates generally to propagation of light, and more particularly to propagation of light that is to be sensed.

Fuhr, P. L., "Measuring with Light", Sensors Magazine Online, May 2000, pp. 1-11, available at www.sensorsmag.com/articles/0500/26/, describes sensors that are sometimes referred to as fiber-optic sensors. Fiber-optic sensors have advantages over conventional electrical- and electromechanical-based sensors, stemming mainly from the fact that the fibers are made of nonconducting glass and photons, not electrons, are the signal propagation elements; as a result, the sensors are immune to electromagnetic interference (EMI) and can operate in harsh environmental conditions, offering a geometric versatility that allows unobtrusive sensing. More than 60 different parameters can be measured using fiber-optic sensors. In extrinsic fiber-optic sensors, the optical fiber acts as a transmit/receive light conduit, with signal modulation occurring outside of the fiber, such as in a modulation region that receives light of known parametric values and provides light with a changed characteristic. In intrinsic fiber-optic sensors, on the other hand, an external perturbation directly interacts with the optical fiber and modulates the light signal in the fiber, such as by changing the optical fiber's waveguide controlling boundary conditions.

Various types of optic-fiber sensors as described by Fuhr have been developed. Many fiber-optic sensors are based on Fiber Bragg Gratings (FBGs), which can be fabricated by exposing a photosensitive optical fiber to a periodic pattern of strong ultraviolet light or by etching a periodic pattern directly into the core of the fiber, forming a periodic modulation of the refractive index along the core. Plastic optical fibers (POF) have been applied to sensing in the form of diffracting structures in single- and multi-mode POF with various fabrication techniques. Photonic crystal sensors are the two- and three-dimensional analogs to FBGs, with a periodic modulation of the refractive index in all directions resulting in special reflection and transmission properties. In addition to other applications, various fiber-optic sensors and other optical sensors have been proposed for use in biosensing.

In fiber-optic sensors that indicate stimulus change in the form of wavelength shift in output light, additional systems have been developed for detecting the wavelength shift. Some examples include a broadband light source in combination with a spectrum analyzer and, alternatively, a tunable laser with a narrow line width, sweeping periodically across the reflectivity peak or resonance dip of the sensor cavity.

Othonos, A., and Kalli, K., Fiber Bragg Gratings, Artech House Publishers, Boston, 1999, pp. 304-330, provide an overview of readout techniques for FBGs.

U.S. Pat. No. 6,785,002 describes a variable filter-based optical spectrometer that uses a tapered Fabry-Perot type linear variable optical filter in conjunction with an optical detector array. The input signal is typically carried on an optical fiber and lenses are used to expand and deliver the essentially point source of light from a fiber end into an optical beam that illuminates the variable filter.

U.S. Pat. No. 5,166,755 describes a spectrometer apparatus in which a spectrum resolving sensor contains an opto-electronic monolithic array of photosensitive elements and a continuous variable optical filter. The filter can include a variable thickness coating formed into a wedge shape on a substrate or directly on the surface of the array. If polychromatic light passes through the variable filter and is spectrally resolved before incidence on the array, the output of all the elements in the array provides the spectral contents of the polychromatic light. High spectral resolving power is obtained by subtracting the output signals of adjacent elements in the array. Non-imaging applications include measurement of spectral transmission through samples; for molecular absorption and emission spectra; for spectral reflectance measurements; for pollution and emission control by measuring transmission or absorption; for astronomical spectral analyses of stellar radiation; for pyrometry by measuring thermal radiation; and underwater spectrometry.

It would be advantageous to have improved techniques for structures that propagate light that is to be sensed.

SUMMARY OF THE INVENTION

The invention provides various exemplary embodiments, including systems, methods, and apparatus. In general, the embodiments involve spreading of light, such as light that is to be photosensed.

These and other features and advantages of exemplary embodiments of the invention are described below with reference to the accompanying drawings.

BRIEF DESCRIPTION OF THE DRAWINGS

FIG. 37 is a graph showing signal response over time for the test implementation of FIG. 36.

FIG. 38 is a graph showing differential signal as a function of temperature for the test implementation of FIG. 37.

DETAILED DESCRIPTION

Figure 1:
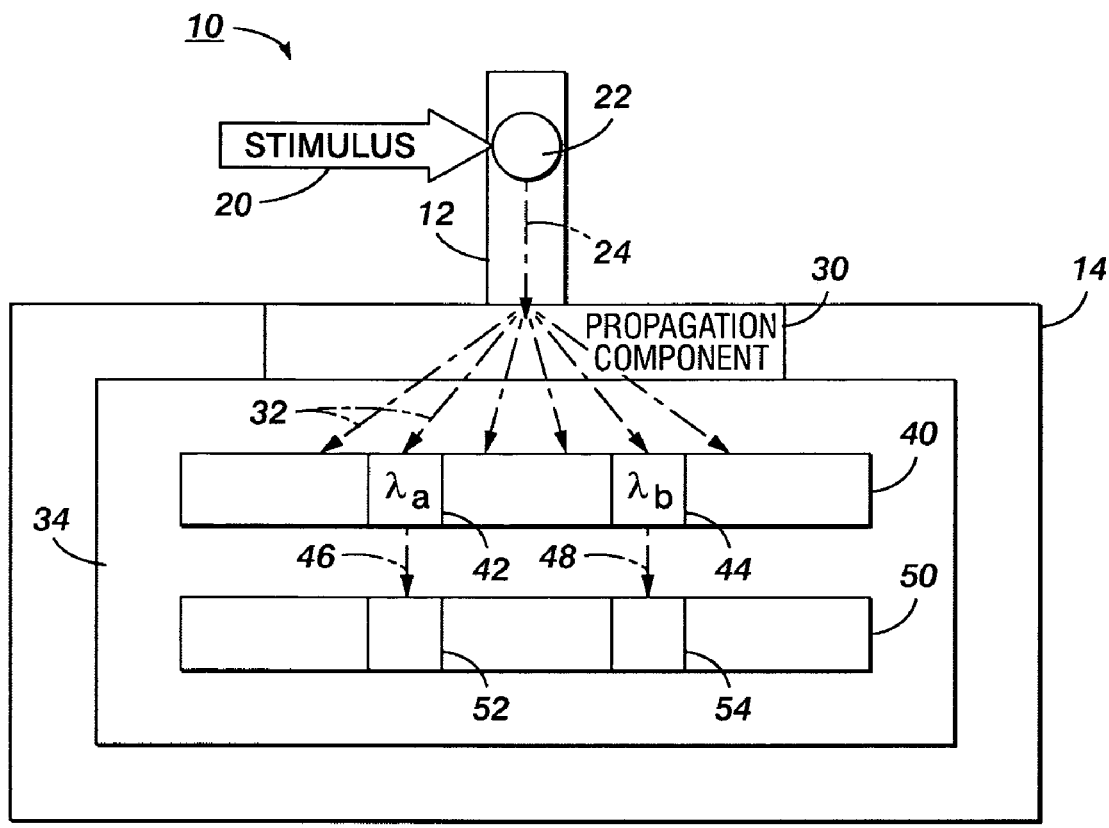
FIG. 1 is a schematic diagram of a stimulus-wavelength converter device with output light being spread as it propagates to a light sensing assembly.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. The term "photon" refers herein to a quantum of light, and the term "photon energy" refers herein to the energy of a photon. Light can be described as having a "photon energy distribution", meaning the combination of photon energies that are included in the light; highly monochromatic light, for example, has a photon energy distribution with one peak energy value.

To "propagate" light through a region or structure is to transmit or otherwise cause the light to propagate through the region or structure. The light may be referred to as "propagated light" or "propagating light".

"Photon energy information" refers herein to information about photon energy, such as information about wavelength, frequency, wavelength shift, frequency shift, or a distribution of wavelengths or frequencies. "Absolute photon energy information" is information about a given photon energy value, such as a specific wavelength or frequency, while "relative photon energy information" is information that relates two photon energy values, whether measured concurrently or at different times.

The interchangeable terms "wavelength shift", "frequency shift", and "photon energy shift" all refer to a shift between photon energies, which is one example of a "change" in photon energy distribution. More generally, a "change" in photon energy distribution occurs whenever a photon energy distribution before an event and a photon energy distribution after the event cannot be made congruent by performing substantially the same normalization at all points in one of the distributions.

The various exemplary implementations described below address problems that arise in reading out photon energy information such as wavelength or wavelength shift information, such as from stimulus-wavelength converters of the types described in the above-cited article by Fuhr and book by Othonos and Kalli. One of those problems is the difficulty of obtaining high relative wavelength resolution rapidly and without bulky, expensive equipment; for example, it is difficult to read out information about very small (e.g. approximately $10^{-4}$ nm to a few nm) wavelength shifts. Another is the difficulty of obtaining high absolute wavelength resolution. It can also be problematic to provide sensitivity to wavelength and not to intensity of incident light.

The term "sensing" is used herein in the most generic sense of obtaining information from a physical stimulus; sensing therefore includes actions such as detecting, measuring, and so forth. To "photosense" is to sense photons, and to "photosense quantity" of photons is to obtain information indicating a quantity of the photons. Photons that are photosensed are sometimes referred to herein as "incident photons".

A "photosensor" is used herein to refer generally to any element or combination of elements that senses photons, whether by photosensing quantity or any other information about the photons. A photosensor could, for example, provide an electrical signal or other signal that indicates sensed information, such as a signal indicating quantity of incident photons. A photosensor that provides electrical signals indicating position, such as of a high-intensity light spot, is referred to herein as a "position sensor". If electrical sensing events occur in a photosensor in response to incident photons, the photosensor may integrate or otherwise accumulate the results of the electrical sensing events during a time period referred to herein as a "sensing period".

In contrast to photosensing, "stimulus-wavelength conversion" refers to a form of sensing that, in response to a stimulus, provides information about the stimulus through photon energies of output light, such as through wavelength or wavelength shift in output light; such information is referred to herein as "wavelength information". The wavelength information can indicate any of various characteristics of the stimulus, such as timing, magnitude, or polarity of a stimulus change, magnitude or polarity of an stable stimulus, and so forth. A "stimulus-wavelength converter" is a sensor that performs stimulus-wavelength conversion.

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange. Where an application requires that a minimum percentage or other proportion of provided photons or sensed quantity of photons have energies within a range or subrange, the minimum percentage or other proportion is referred to herein as the "application's minimum photon proportion".

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations described herein include features characterized as "cells" and "arrays", terms that are used with related meanings: An "array" is an arrangement of "cells". An array on an IC or other support surface may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

A "photosensor array" is an array in which some or all of the cells are or include photosensors. Accordingly, an IC "includes" a photosensor array if the IC includes an array of cells, and at least some of the cells include respective photosensors. A cell that includes a photosensor may also include "cell circuitry", such as circuitry that makes connections with the photosensor, that transfers signals to or from the photosensor, or that performs any other function other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application of an IC that includes a photosensor array, circuitry that "responds to" one or more photosensors can be any circuitry that, in operation, receives information from the photosensors about their photosensing results through an electrical connection. Circuitry that responds to a photosensor could be circuitry in the same cell as the photosensor, or it could be array circuitry, peripheral circuitry, or other external circuitry, or it could include any suitable combination of cell circuitry, array circuitry, peripheral circuitry, and other external circuitry.

Figure 2:
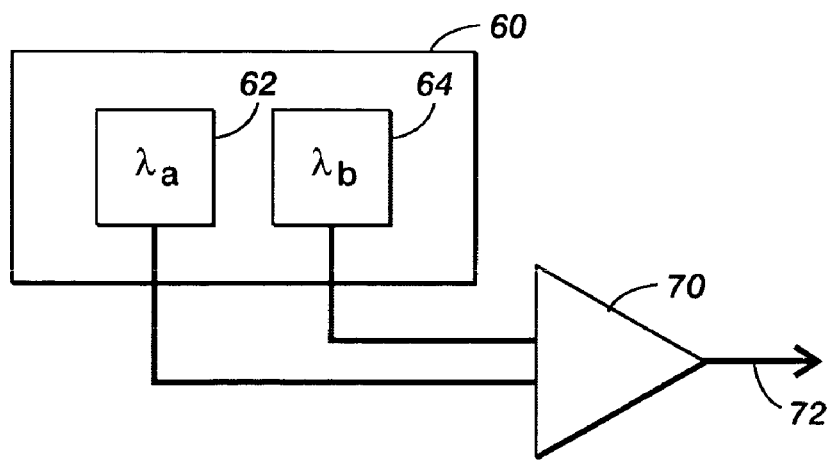
FIG. 2 is a schematic top view of a photosensor array that could be used in the light sensing assembly of FIG. 1.

FIGS. 1 and 2 illustrate general features of a stimulus-wavelength conversion device 10. Device 10 includes stimulus-wavelength converter 12 and readout components 14.

As schematically shown by arrow 20 in FIG. 1, converter 12 receives a stimulus, such as the presence, absence, quantity, or concentration of an analyte. Within converter 12, an interaction occurs in response to the stimulus, as represented schematically by circle 22, with the result that output light, represented by ray 24, includes wavelength information or other photon energy information about the stimulus. Specifically, the output light could undergo a wavelength shift in response to a change in the stimulus. The stimulus could be any of a multitude of types, including but not limited to temperature, pressure, stress, strain, flow, level, speed or rpm, position, orientation, motion, acceleration, presence or absence of an analyte, rain, thickness, liquid quality, breakage, or magnetic field.

Within converter 12, the stimulus could affect photon energies in the output light in any of numerous ways, some of which are described in the above-cited article by Fuhr and book by Othonos and Kalli. For example, converter 12 could include a surface or point at which broadband input light is partially reflected to provide output light, as can occur in an FBG or photonic crystal sensor. Or light could be generated within converter 12 to provide output light, as can occur in a laser cavity. Or fluorescence within converter 12 could provide output light. Or broadband input light could be transmitted through a Fabry-Perot-type structure to provide output light. In each case, the stimulus affects photon energies in the output light from converter 12; for example, the stimulus could affect the laser cavity, could be presence or absence of a fluorescent analyte, or could change the cavity of the Fabry-Perot structure.

Readout components 14 could be implemented in many ways, and FIG. 1 illustrates some components that may occur in exemplary implementations. Propagation component 30 receives output light from converter 12 and propagates the output light to other components, as suggested by rays 32.

As used herein a "light propagation component" or simply "propagation component" is any feature, surface, interface, layer, lens, transmission structure as described below, or other component that provides light in response to received light. In general, a light propagation component has an "entry surface", meaning a surface at which it receives entering light, and an "exit surface", meaning a surface at which it provides exiting light. Between its entry and exit surfaces, a propagation component can perform one or more functions on the light, including transmitting, guiding, collimating, imaging, focusing, spreading, and so forth. For example, a propagation component could include one or more optical fibers to transmit output light from converter 12 between its entry surface and an assembly of other components at its exit surface.

In the example illustrated in FIG. 1, rays 32 diverge within component 30, suggesting that component 30 spreads output light from converter 12, but component 30 could direct the output light in any other appropriate way, as illustrated in greater detail by examples set forth below. As used herein a "light spreading component" or simply "spreading component" is a propagation component for which the exiting light's intensity distribution at any given time has a greater variance in at least one direction than the entering light to which it responds, where variance is expressed as a distance across the respective surface. The exiting light from a spreading component can be described as "spreaded" over a greater extent of the exit surface than the entering light occupies in the entry surface, though the entry and exit surfaces may be closely spaced surfaces in some implementations. Spreading can also be described as occurring "in a" direction, meaning that increase in variance occurs in the direction; a direction in which spreading occurs may be straight, but rather could be curved or angled.

Light sensing assembly 34 receives the output light, such as after spreading by component 30, and, in response, provides electrical signals that indicate information about the stimulus. Assembly 34 illustratively includes laterally varying transmission structure 40. A structure that "transmits" photons, sometimes referred to herein as a "transmission structure", is any material structure through which light can propagate. It is not necessary that there be a one-to-one relationship between photons that enter a transmission structure and photons that exit from it as long as the structure provides exiting photons in response to entering photons as a result of light propagation through the structure.

More generally, to "transmit" photons is to perform a function by which exiting photons at an exit position are provided in response to entering photons at an entry position as a result of light propagation between the entry and exit positions. To "transmit only" a specified set of photons from a first position to a second refers to a function that transmits photons from the first position to the second, but predominantly photons in the specified set. As with providing photons and photosensing, described above, if a transmission structure transmits only a specified set of photons, between 60-90% of the transmitted photons are in the specified set, but the percentage could be lower or higher. In some applications, 90% or even 95% or more of the photons are in the specified set.

One type of transmission structure is a "coating", meaning a layered structure of light-transmissive material that is on or over another component such as a photosensor array or position sensor. Various examples of coatings are described below.

A transmission structure provides (and a photosensor receives from a transmission structure) photons "throughout", "within", or "in" a range or subrange if the provided photons are predominantly within the range or subrange. As in other contexts described above, between 60-90% of the photons from a transmission structure typically have energies within the range or subrange, but the percentage could be lower or higher. In some applications, 90% or even 95% or more of the photons have energies within the range or subrange.

A transmission structure can be characterized by an "energy transmission function" or simply "transmission function" that relates positions in the transmission structure to photon energies that are transmitted at the positions. For example, if a position transmits photons within a specific subrange but not outside the specific subrange, the transmission function at that position passes the specific subrange but not other subranges.

A transmission structure is "laterally varying" if its transmission function varies as a function of position within its exit surface, such position being referred to herein as "lateral position". The variation in transmission function can, for example, vary according to a gradient, which can be a "constant transmission gradient" if it varies continuously or uniformly in a lateral direction or a "step-like transmission gradient" if it varies in a step-like manner in a lateral direction. Where a transmission structure is two-dimensional, it could have a constant transmission gradient in one lateral direction and a step-like transmission gradient in another. In general, a transmission function "varies in a" direction if it varies along a line that extends in the direction; a direction in which a transmission function may be straight, but rather could be curved or angled.

In addition to having a laterally varying energy transmission function, a transmission structure may also transmit light as a function of incident angle. This can also be a source of lateral inhomogeneity in transmission, for example, of light from a point-like source, because the light will have different incident angles at different positions on the transmission structure's entry surface. A transmission structure may therefore be described as "laterally inhomogeneous" if it has a laterally varying energy transmission function, if it transmits light as a function of incident angle, or both.

Structure 40 transmits photon energies as a function of lateral position and therefore is laterally inhomogeneous. This feature is illustrated in FIG. 1 by regions 42 and 44 in structure 40. As shown, region 42 transmits light in a subrange centered about wavelength $\lambda_a$. Similarly, region 44 transmits light in a subrange centered about wavelength $\lambda_b$. As a result, the light from regions 42 and 44, represented respectively by rays 46 and 48, is incident on photosensing components 50 at different positions, represented respectively by position 52 and position 54. Therefore, if a change in the stimulus causes a change in photon energy between $\lambda_a$ and $\lambda_b$, this change will be indicated by a change in the light detected at positions 52 and 54.

FIG. 1 therefore illustrates the importance of spreading light to be sensed by assembly 34: If the output light from converter 12 were not spreaded over the entry surface of transmission structure 40, but were instead incident only on a small area of transmission structure 40, the light would only reach a corresponding small area of photosensing components 50. In this case, the wavelength information that would otherwise be sensed in other areas of photosensing components 50 would be lost. In other words, spreading is necessary so that photosensing components 50 can provide signals that accurately indicate wavelength information from the output light.

Photosensing components 50 could be implemented in many ways, including with various ICs that include photosensor arrays or position sensors. FIG. 2 shows array 60, an example of a photosensor array that could implement photosensing components 50.

Array 60 in FIG. 2 includes cells 62 and 64, labeled to show that cell 62 is at position 52 in FIG. 1, and therefore receives predominantly light in a subrange around wavelength $\lambda_a$, while cell 64 is at position 54 and receives predominantly light in a subrange around wavelength $\lambda_b$. Output light from converter 12 could, for example, have or be provided about one or more "peak energy values" in a given application, meaning central values of photon energy subranges in which intensity can significantly exceed intensities in nearby subranges. If the output light has two peak energy values $\lambda_a$ and $\lambda_b$ for two respective values of stimulus 22 (e.g. presence and absence, two quantities, or two concentrations of an analyte), then a change between the stimulus values would result in a wavelength shift between $\lambda_a$ and $\lambda_b$, resulting in a change in quantities of photons sensed by cells 62 and 64. Similarly, output light from converter 12 could be in a "narrow band" of energies in a given application if it has a peak energy value and the subrange in which intensity significantly exceeds nearby intensities is approximately one-tenth or less of the application's energy range; in contrast, "broadband" generally refers to light that has an energy distribution that is more uniform than narrow band light across a relatively broad energy range and that contains a significant light intensity in all energy subranges of interest.

More generally, a wavelength shift between wavelengths $\lambda_a$ and $\lambda_b$ or another change in photon energy distribution at the input surface of transmission structure 40 can change "relative quantities" of photons provided at positions 52 and 54, meaning that the quantities provided at the two positions have a different relation to each other after the shift than they did before it. For example, the quantities could increase or decrease, but by amounts such that the quantity at one position becomes a larger or smaller fraction of the quantity at the other position; the quantity at one location could change from being less than the quantity at the other position to being greater; or one quantity could increase while the other decreases; etc.

FIG. 2 also shows how the quantities of photons sensed by cells 62 and 64 can be compared, such as by comparator 70. Comparator 70 could, for example, be biased so that the output signal on line 72 indicates a stimulus change of a particular type that causes a wavelength shift between wavelengths $\lambda_a$ and $\lambda_b$.

As used herein, an operation or a component of circuitry "compares" if the result indicates a relationship between signals or values being compared, such as difference, equality, which is greater, which is less, whether the difference is greater or less than a quantity or meets some other criterion, and so forth.

If it indicates the difference between the photosensed quantities of cells 62 and 64, the value of the output signal on line 72 would be an example of a "differential quantity", which refers herein to a value that indicates a difference between two quantities. A differential quantity could, for example, be an unbiased or biased analog output value from a differential amplifier or other analog comparator; a simple difference obtained by subtraction of two digital values, one or both of which could be normalized or otherwise adjusted; a ratio obtained by analog or digital circuitry; a value obtained by combining related differential quantities, such as differences between each quantity and a third quantity; or any other analog or digital value that includes information about the difference. A "differential signal" generally refers herein to a signal that indicates a differential quantity.

Although represented in FIG. 1 simply as a box, converter 12 could be implemented in numerous ways, including FBGs, POFs, photonic crystals, and various optical biosensors, as mentioned above. As described in greater detail below, however, the design of readout components 14 depends primarily on the properties of output light from converter 12, such as whether it is monochromatic or broad spectrum and whether it is parallel or divergent. Other factors affecting the design of readout components 14 include wavelength resolution and energy range.

If converter 12 is a single fiber with a single FBG, the output light will be point-like and monochromatic. For this type of sensor, propagation component 30 can spread the output light over substantially the whole area of laterally varying transmission structure 40, so that the position of the transmitted light spot on photosensing components 50 corresponds with the wavelength of the output light. Photosensing components 50 could be implemented as a one-dimensional photosensor array with a coating as described below. In addition, photosensing components 50 could alternatively be implemented as a position sensor, as described in co-pending U.S. patent application Ser. No. 10/922,870, entitled "Chip-size Wavelength Detector" and incorporated herein by reference in its entirety.

If converter 12 is a single fiber with multiple FBGs, it can provide a point-like output light with multiple photon energies. As in the previous example, propagation component 30 can spread the output light over substantially the entire area of laterally varying transmission structure 40, and photosensing components 50 can be implemented with an array like photosensor array 60, with each cell sensitive to a respective energy subrange. More specifically, photosensing components 50 can be implemented with a one-dimensional photosensor array with a coating as described below.

If converter 12 is a fiber bundle with a single FBG in each individual fiber, the output light will include several monochromatic point-like outputs. Propagation component 30 can spread the light from each point-like output over a respective region of laterally varying transmission structure 40. Cross-talk between the different light outputs can be minimized by special optics or blades as described below. For each region of transmission structure 40, photosensing components 50 can include a respective set of sensing locations. Photosensing components 50 could be implemented, for example, as a two-dimensional photosensor array with a coating as described below. Alternatively, a coated position sensor array could be used, containing a number of position sensor elements as described in co-pending U.S. patent application Ser. No. 10/922,870, entitled "Chip-size Wavelength Detector" and incorporated herein by reference in its entirety. These techniques may also be appropriate for a converter that provides a single point-like output with a very large photon energy range.

If converter 12 is a fiber bundle with multiple FBGs per fiber, the output light will include several point-like outputs, each with multiple photon energies. Propagation component 30 can spread the light from each output over structure 40 such that one respective row of a photosensor array within components 50 receives the light from each output. Photosensing components 50 could be implemented as a two-dimensional photosensor array or CCD IC with a coating as described below. Cross-talk between the different light outputs can be minimized by special optics or blades as described below. These techniques may also be appropriate for a converter that provides a single point-like output with a very large photon energy range.

Converters can provide output light in various ways other than by fiber end facets and point-like sources. As described below, for example, a converter may provide output light through a broad area source other than a fiber end facet, where the term "broad area source" means a source that has sufficient two-dimensional extent that it cannot be approximated by a single point-like source. Techniques as described below could be applied, for example, to a broad area source that provides substantially the same photon energy distribution throughout its area. In some techniques, a broad area source could be attached directly to light sensing assembly 34.

The principles set forth above can also be applied to converters other than FBGs, such as POFs, photonic crystals, and optical biosensors. In each case, an appropriate combination of components can be used to obtain satisfactory sensing and readout.

Photosensing components 50 can include various photosensitive elements, chosen to be appropriate for the incident light intensity. For low power incident light, exemplary solutions include: (1) a small detector surface area, which is beneficial because the total light is not distributed over a large area and the intensity per unit area stays high—this solution is also inexpensive, but, due to a limited detector size, the wavelength range and resolution may also be limited; (2) arrays such as cooled CCDs, avalanche photodiodes, and photomultiplier tubes (PMTs) that provide increased signal-to-noise ratio but are expensive; or (3) intensified CCD arrays that enable single photon counting but are very expensive.

Figure 3:
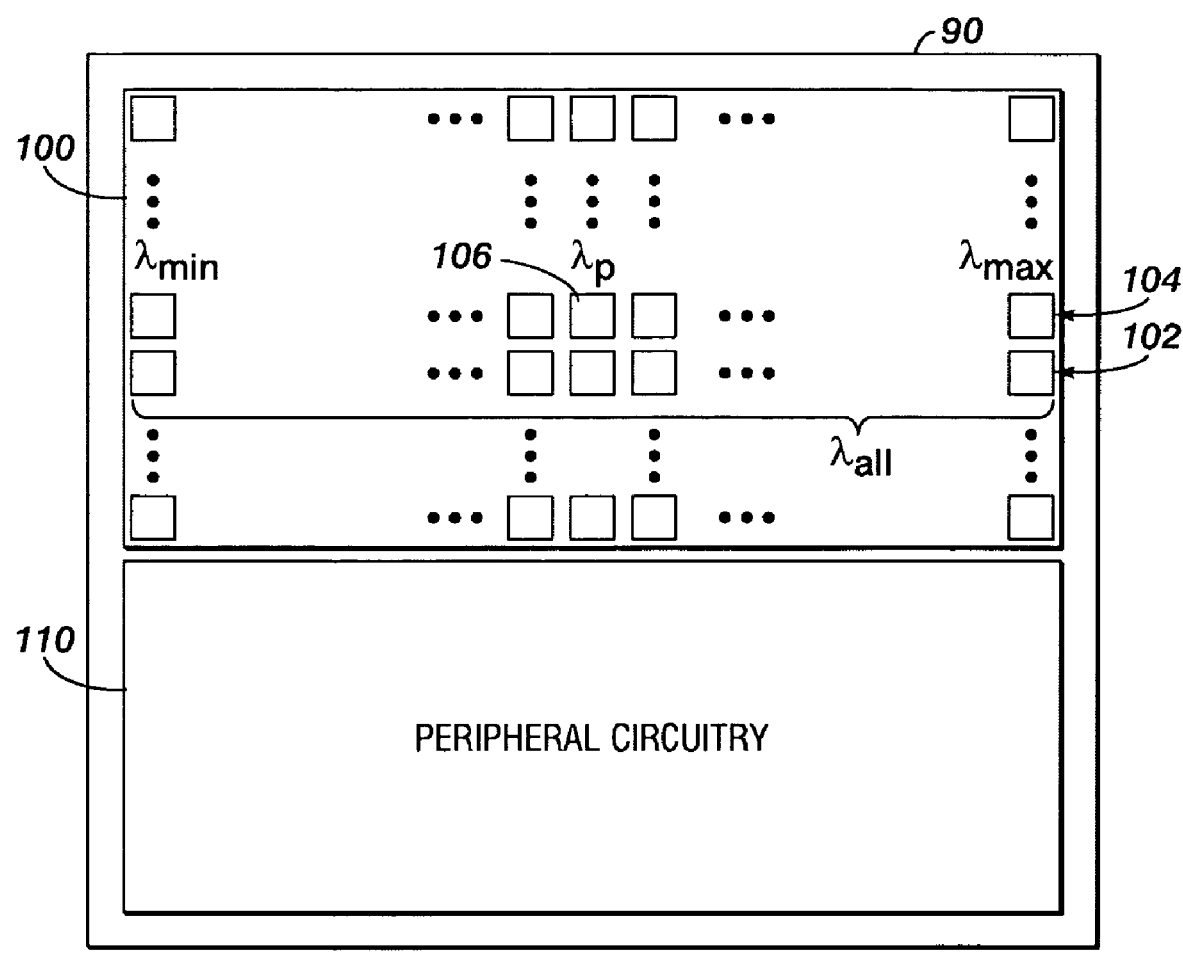
FIG. 3 is a schematic plan view of an integrated circuit (IC) with a photosensor array that can be used in the light sensing assembly of FIG. 1.

Light sensing assembly 34 in FIG. 1 can therefore be implemented in a wide variety of ways, including various types of photosensor arrays and position sensors. FIG. 3 is a schematic view of an exemplary IC with a photosensor array that can be used in some such implementations. FIGS. 4-11 illustrate various implementations of assembly 34 that can include an IC like that shown in FIG. 3, or that could alternatively be implemented with position sensors as described in co-pending U.S. patent application Ser. No. 10/922,870, entitled "Chip-size Wavelength Detector" and incorporated herein by reference in its entirety.

IC 90 in FIG. 3 includes photosensor array 100, which is illustratively a two-dimensional array, with at least two rows of cells that include photosensors. Different rows or other parts of array 100 can be provided with different coatings or can be otherwise structured so that their cells photosense different ranges or subranges of photon energies. As a result, the information obtained from a single IC can provide a detailed analysis of incident photons over a broad range of photon energies. In addition, reference cells, such as the cells in row 102, can be used to provide a spatially resolved real-time reference signal.

Within an array, a "pair" of cells is any two cells; unless otherwise specified, the cells in a pair need not have any other specific relationship to each other. The cells in a pair are "near each other" if the distance between them meets a suitable criterion for nearness, such as being no greater than ten times the maximum diameter of the larger of the cells. In general, for example, two cells that are adjacent are also near each other. More generally, a set of cells are all "nearby" another cell if each cell in the set and the other cell, taken as a pair, are near each other. A feature of array 42 is that it includes one or more reference cells that are nearby to a subrange cell, such as by being adjacent to the subrange cell.

Each cell in row 102 photosenses photons throughout a suitable range, characterized as $\lambda_{all}$, to produce a reference for a nearby cell in row 104. For implementations in which it is advantageous to have signal strengths of the same order from a cell in row 102 and its paired cell in row 104, the cell in row 102 must be different from the cells in row 104. For example, it could have a different sensing area or it could have a gray filter coating different than a coating over the paired cell in row 104.

Each cell in row 104, on the other hand, photosenses a respective subrange between $\lambda_{min}$ and $\lambda_{max}$, with illustrative cell 106 photosensing a subrange centered around $\lambda_p$. IC 90 also includes array circuitry (not shown) as well as peripheral circuitry 110 which perform various functions relating to readout of photosensed information from array 100.

One advantage of the technique illustrated in FIG. 3 is that IC 90 provides a compact photosensor array that can be used within a device, such as in a stimulus change sensing device. Results from more than one such IC within a device may be combined to obtain more complete sensing. In general, photosensed quantities or other results of photosensing are "combined" when they are included together in any data structure or signal, possibly after one or more data processing or signal processing operations.

Figure 4:
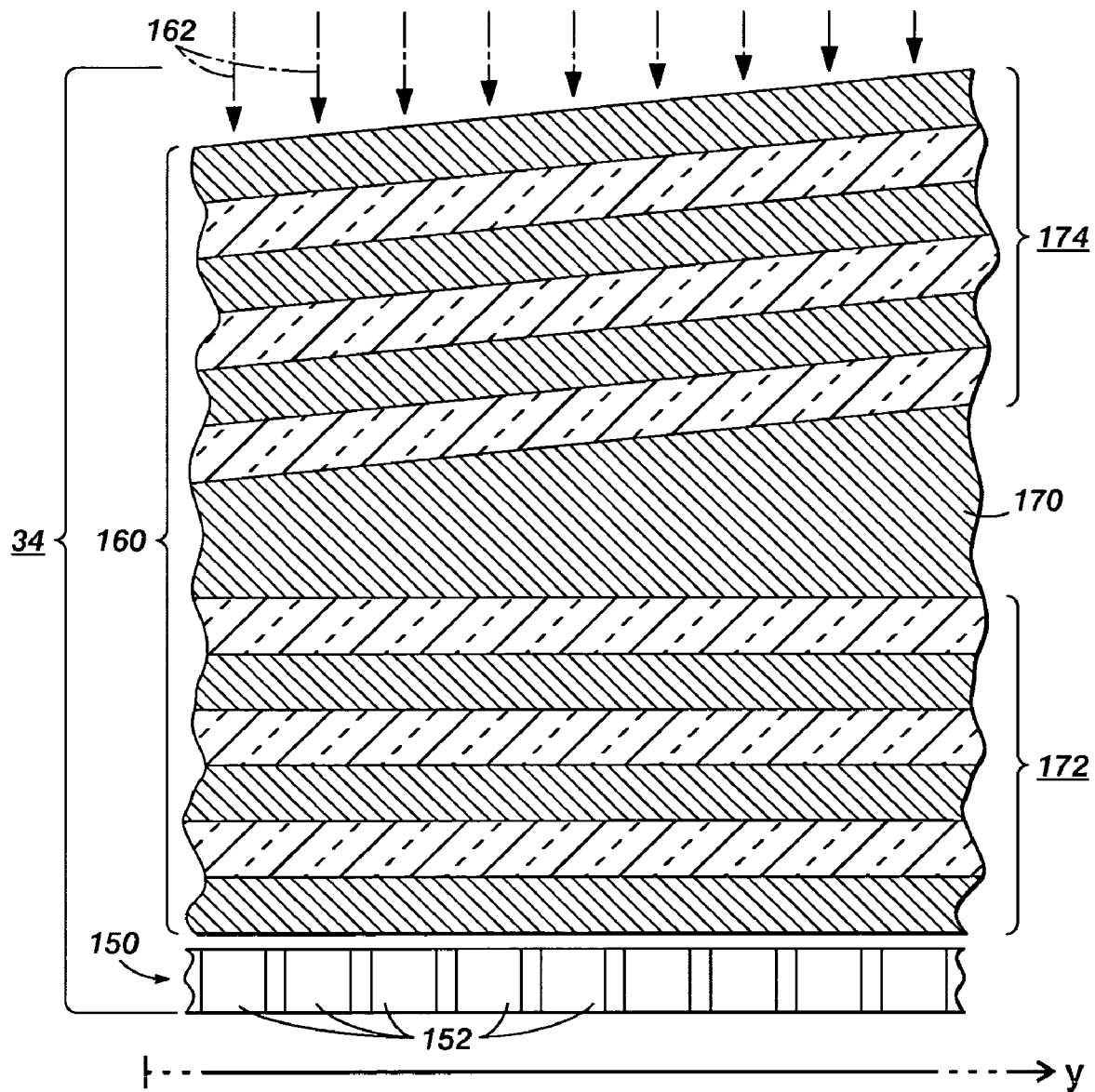
FIG. 4 is a schematic cross-sectional view of an implementation of an assembly that can be used in FIG. 1.

FIG. 4 illustrates an implementation of assembly 34, showing in greater detail how cells of an array photosense subranges, such as in row 104 in FIG. 3. As in other implementations described herein, assembly 34 in FIG. 4 can be supported by a suitable support component.

In FIG. 4, a cross-section has been taken through a fragment 150 of a photosensor array, with cells 152 of the fragment 150 shown schematically in cross-section. Over cells 152 is a transmission structure 160 that receives incident light 162, such as from any of the below-described implementations for receiving light from a stimulus-wavelength converter.

Transmission structure 160 can, for example, be a film with laterally varying light transmission properties as described, for example, in co-pending U.S. patent application Ser. No. 10/922,870, entitled "Chip-size Wavelength Detector" and incorporated herein by reference in its entirety. In the portion of transmission structure 160 shown in FIG. 4, wedge-shaped transmissive cavity 170 is enclosed between reflective films 172 and 174, forming a wedge-shaped Fabry-Perot etalon. Because its thickness varies as a function of position along the y-axis, transmission structure 160 will transmit different wavelengths as a function of position along the y-axis. Such a function is sometimes referred to herein as a "wavelength-position function".

Transmission structure 160 can be produced with appropriate coatings on or over a photosensor array. Films 172 and 174 and cavity 170 could all be produced, for example, by exposure to deposition beams in an evaporation chamber; films 172 and 174 with uniform thicknesses could be produced by appropriate on-axis deposition, while cavity 170 with laterally varying thickness can be produced by appropriate off-axis deposition. FIG. 4 illustratively shows films 172 and 174 as relatively thick compared to cavity 170, which would be appropriate for layers of non-metallic material such as $SiO_2$, $TiO_2$, or $Ta_2O_5$, with thicknesses designed as described below; such materials are typically used to produce Bragg mirrors by depositing thin alternating layers with low absorption coefficients and large differences in refractive indices. If films 172 and 174 are reflective metal, however, they could be much thinner.

For an implementation with non-metallic material, specific thicknesses of cavity 170 and films 172 and 174 could be designed from the desired transmitted wavelength $\lambda$ and the refractive index n of cavity 170. The thickness of cavity 170 is typically chosen to be $\lambda/(2n)$ or an integer multiple thereof, while the thicknesses of Bragg mirror layers within films 172 and 174 are typically $\lambda/(4n)$. The number of pairs of such layers in each of films 172 and 174 can vary between a few (e.g. 2-5) all the way up to 20 or 30, depending on the difference in refractive index between the two materials used, the desired transmission band width, and the desired stop band reflectivity. Therefore, in typical implementations, films 172 and 174 are much thicker than cavity 170, as suggested in FIG. 4.

Figure 5:
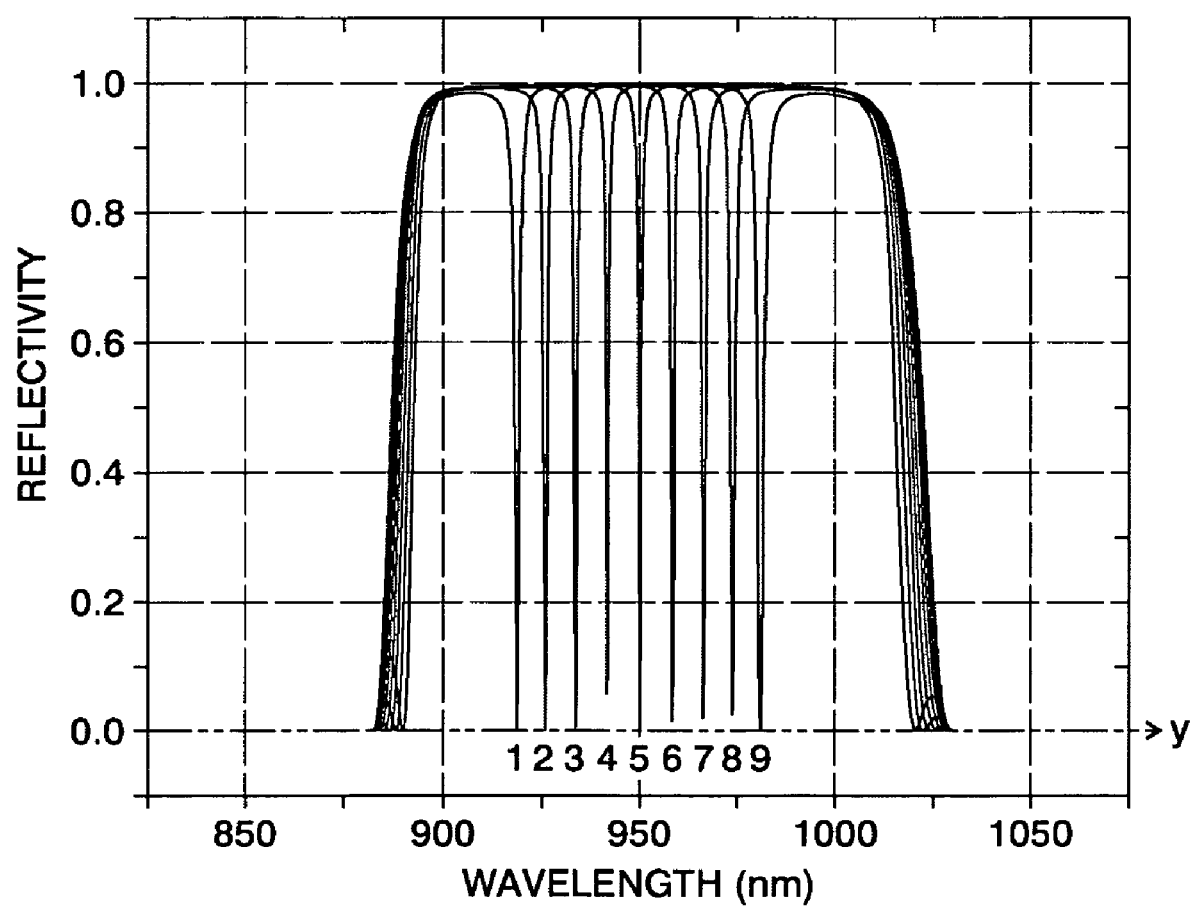
FIG. 5 is a graph illustrating laterally varying light transmission properties of a transmission structure as in FIG. 4.

FIG. 5 illustrates the laterally varying light transmission properties of transmission structure 160. Because its thickness varies as a function of position along the y-axis, cavity 170 transmits different wavelengths as a function of position along the y-axis. Wavelengths of photons predominantly transmitted to nine of cells 152 as in fragment 150 are illustrated by the low reflectivity minima labeled 1 through 9. As can be seen, the high-transmissivity photon energy range for transmission structure 160 varies laterally.

Figure 6:
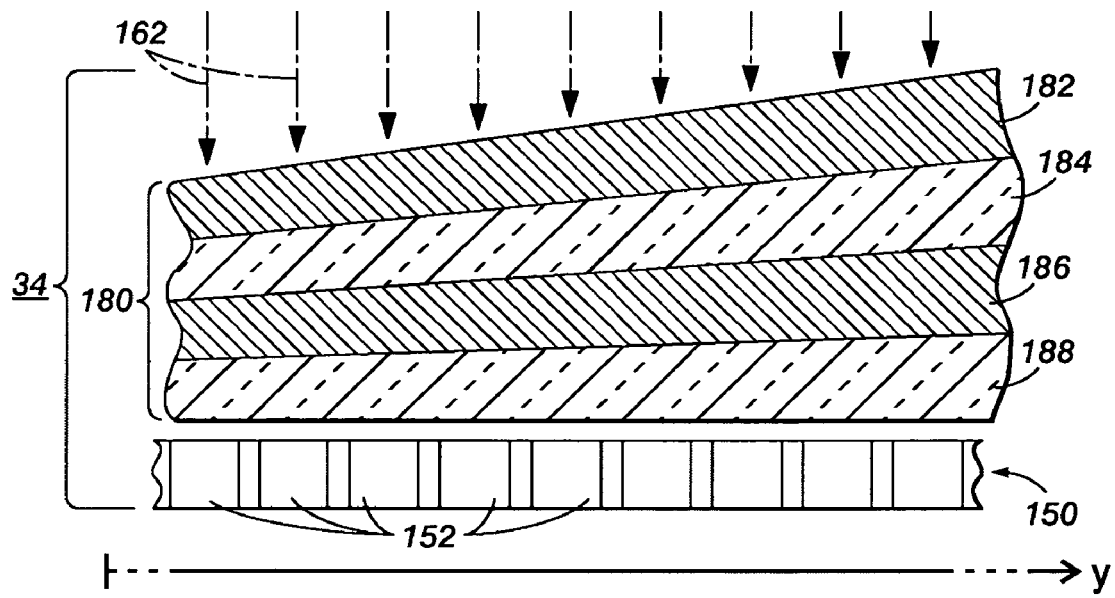
FIG. 6 is a schematic cross-sectional view of another implementation of an assembly that can be used in FIG. 1.

FIG. 6 illustrates another implementation of assembly 34, with features that have the same reference numbers as in FIG. 4 being implemented as described above. Rather than transmission structure 160, however, assembly 34 includes transmission structure 180. Transmission structure 180 can, for example, be a laterally graded Bragg mirror in which each of layers 182, 184, 186, and 188 is laterally graded. Each of layers 182, 184, 186, and 188 could be produced as described above for cavity 170, using off-axis deposition in an evaporation chamber.

Figure 7:
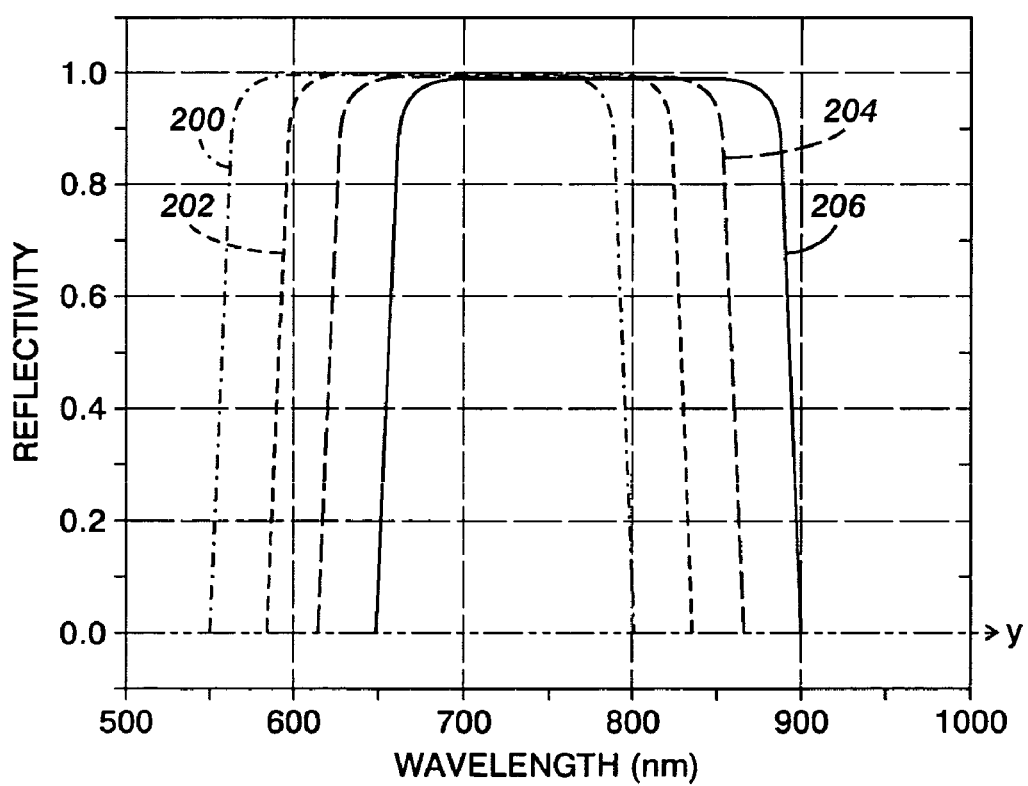
FIG. 7 is a graph illustrating the laterally varying light transmission properties of a transmission structure in FIG. 6.

FIG. 7 illustrates the laterally varying light transmission properties of transmission structure 180. Because its thickness varies as a function of position along the y-axis, transmission structure 180 reflects different wavelengths as a function of position along the y-axis. Curves 200, 202, 204, and 206 are shown, representing reflectivity of the portion of transmission structure 180 over each of four cells 152 in fragment 150, with curve 200 being for the leftmost cell of the four in FIG. 6 and curve 206 being for the rightmost cell of the four. As can be seen, the high-reflectivity photon energy range for transmission structure 180 varies laterally.

Figure 8:
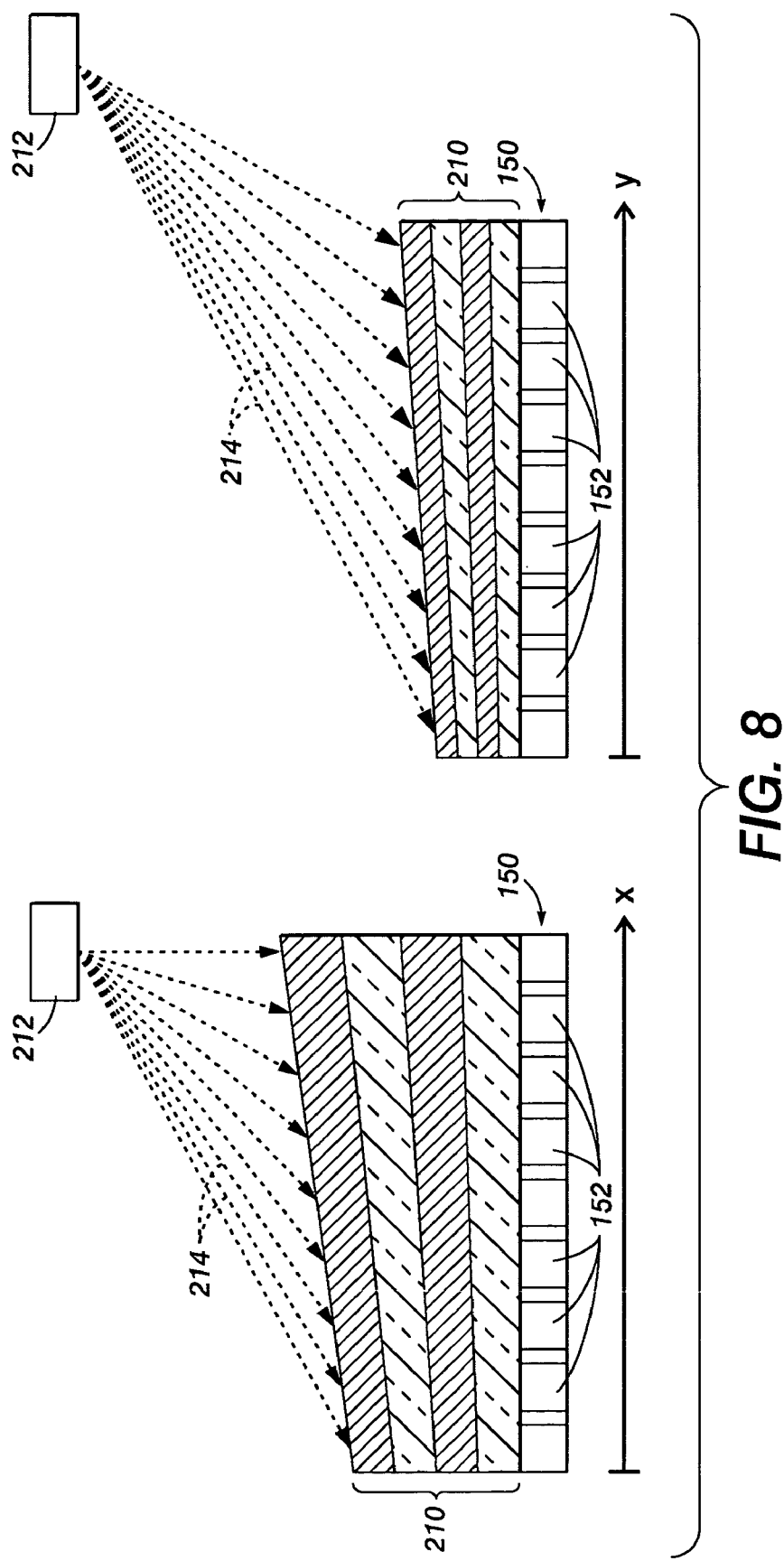
FIG. 8 illustrates a technique that produces a transmission structure that can be used in an assembly as in FIG. 1, showing orthogonal schematic cross-sectional views of deposition.

FIG. 8 illustrates a technique that produces transmission structure 210 with laterally varying light transmission properties similar to those illustrated in FIGS. 5 and 7 but with lateral variation in each of two dimensions. This technique can be used to produce different coatings for different rows of a photosensor array so that their cells photosense different ranges or subranges of photon energies, and can be used separately or in combination with reference cells.

Transmission structure 210 is produced on or over cells 152 of photosensor array 150 by using deposition source 212 to provide deposition beam 214 that can be characterized at any given point on the surface of structure 210 by two angles. One of the two angles results from angular variation of deposition beam 214 in the x-direction across array 150, while the other results from angular variation in the y-direction. As a result, the thickness gradient of structure 210 is similarly different in the x- and y-directions. Therefore, cells within each row extending in the y-direction will photosense a range of photon energies similarly to FIG. 7, but the range will be different than the range photosensed by cells in any other row extending in the same direction.

The technique of FIG. 8 could be implemented in a variety of ways. For example, during deposition, structure 210 could be formed on a support structure that is tilted as required, deposition source 212 could be tilted as required, or both kinds of tilt could be employed.

Figure 9:
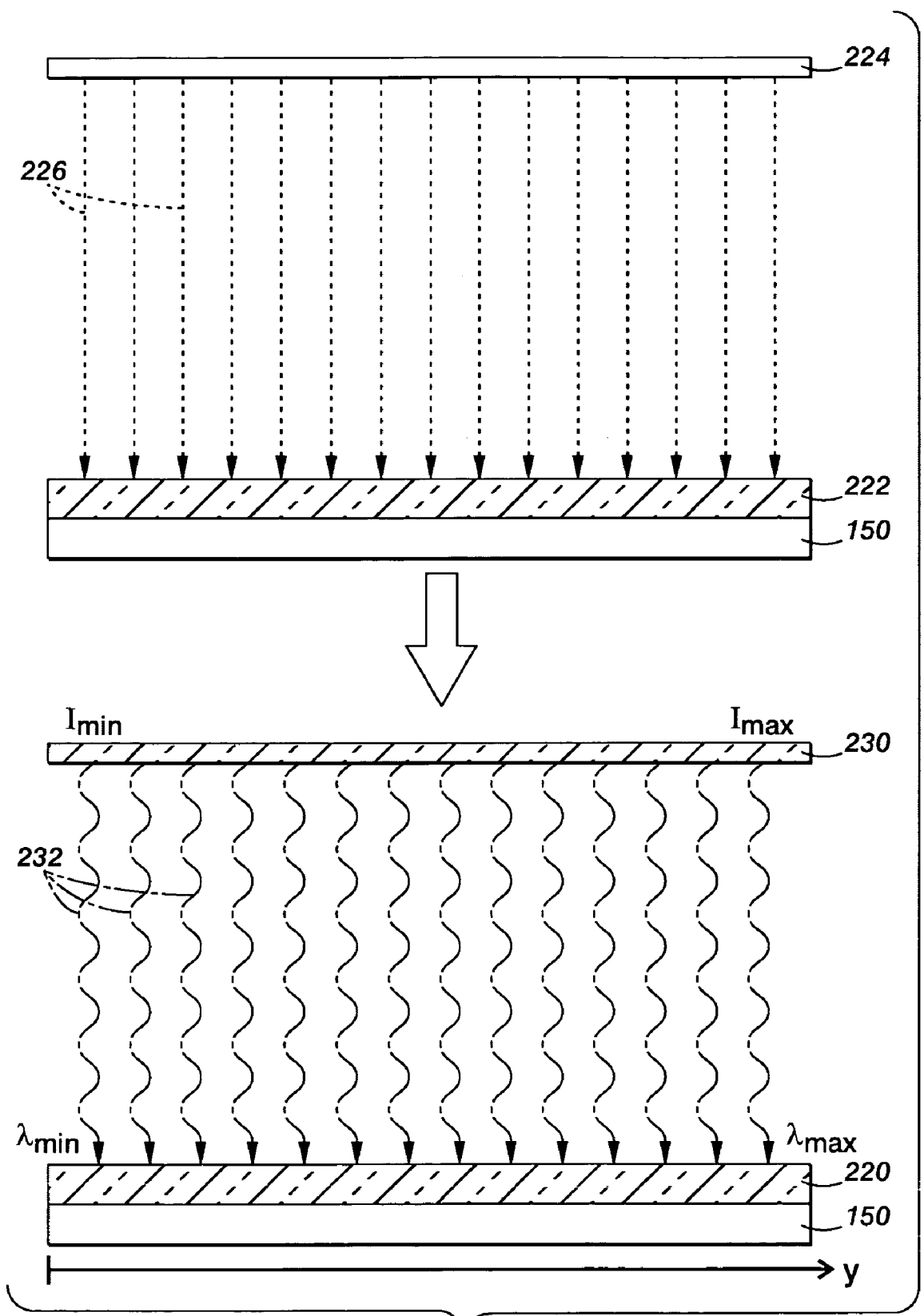
FIG. 9 illustrates another technique for producing a transmission structure that can be used in an assembly as in FIG. 1, showing two schematic cross-sectional views of stages of the technique.

FIG. 9 illustrates a technique that produces transmission structure 220 with laterally varying light transmission properties similar to those illustrated in FIGS. 5 and 7 but without variation in thickness of transmission structure 220. The technique in FIG. 9 can be characterized as providing laterally varying optical thickness d*n, where d is thickness and n is index of refraction, but without actual variation in thickness d. In contrast, the techniques of FIGS. 4-8 provide varying optical thickness by providing actual variation in thickness.

In the upper part of FIG. 9, homogeneous coating 222 is deposited by deposition source 224, which provides deposition beam 226 uniformly over the surface of photosensor array 150 similar to those in FIGS. 4, 6, and 8. This operation could, for example, be implemented with conventional deposition techniques.

Then, in the lower part of FIG. 9, light source 230 is scanned across the coating over array 150 to introduce a laterally varying change of refractive index in resulting transmission structure 220. For example, source 230 can be an ultraviolet source that provides intensity I with a constant value along each line parallel to the x-axis (perpendicular to the plane of FIG. 9), but varying from $I_{min}$ for lines nearer the x-axis to $I_{max}$ for lines farther from the x-axis, as shown in FIG. 9 by the values along the y-axis. As a result, the wavelengths transmitted to cells in array 150 can vary along the y-axis from $\lambda_{min}$ to $\lambda_{max}$, as shown. The same pattern of intensity can be concurrently applied by source 230 to each of a number of arrays that are appropriately arranged, allowing batch fabrication of arrays. Two-dimensional variation in optical density equivalent to that in FIG. 8 could also be obtained with two-dimensional variation in the ultraviolet source's intensity.

Figure 10:
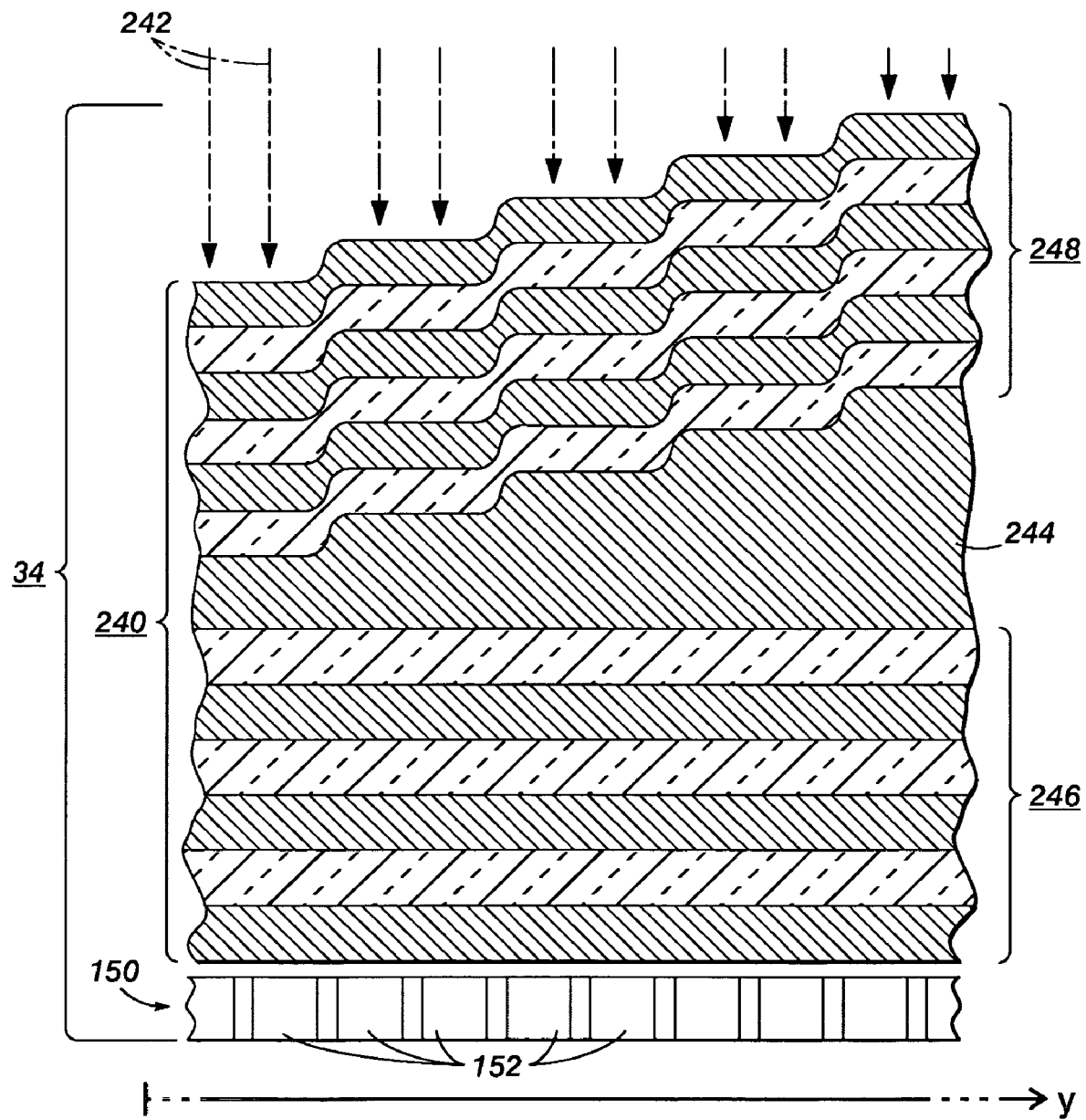
FIG. 10 is a schematic cross-sectional view of another implementation of an assembly that can be used in FIG. 1.

FIG. 10 illustrates an implementation of assembly 34 that is similar to the implementation of FIG. 4, but with a step-like gradient in the y-direction which could be combined with a constant thickness in the x-direction or with a constant gradient in the x-direction as in the left-hand side of FIG. 8. The arrangement in FIG. 10 can be used with a photosensor array that has discrete photosensing cells, as illustrated by fragment 150 with cells 152. If used with a CCD or CMOS photosensor array, cells under different steps will receive photons in different energy subranges of the range of photon energies incident upon assembly 34.

In FIG. 10, in addition to the cross section through fragment 150, a cross section has been taken through transmission structure 240 that receives incident light 242, such as from any of the below-described implementations for receiving light from a stimulus-wavelength converter. Similarly to transmission structure 160 in FIG. 4, transmission structure 240 includes staircase-shaped transmission cavity 244 enclosed between reflective films 246 and 248, forming a staircase-shaped Fabry-Perot etalon. Because its thickness varies as a function of position along the y-axis, transmission structure 240 will transmit different wavelengths as a function of position along the y-axis.

Figure 11:
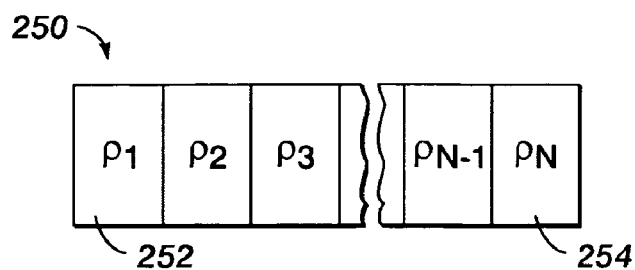
FIG. 11 is a schematic top view of a mask that could be used to produce a transmission structure as in FIG. 10.

FIG. 11 illustrates half-tone mask 250 that can be used in producing transmission structure 240. For example, the technique in FIG. 9 could be modified by interposing mask 250 between deposition source 224 and array 150 while depositing cavity 244 so that, rather than being homogeneous in thickness, coating 222 would have a step-like shape like structure 240 in FIG. 10. As shown, mask 250 includes a series of N rectangular regions 252 through 254, each of which has holes large enough that material from deposition beam 226 can easily pass through. The density of the holes increases, however, from $\rho_1$ to $\rho_N$, so that the thickness of cavity 244 also increases, and cavity 244 is thinnest under region 252, becomes thicker under each successive region, and is thickest under region 254.

This technique can also be applied to achieve a continuous or uniform cavity gradient as depicted in FIG. 4. In this case, the density of holes would increase continuously from $\rho_1$ to $\rho_N$, so that the thickness of cavity 170 also increases gradually, and cavity 170 is thinnest at the left side of structure 160 and thickest and the right side of structure 160.

A transmission structure of uniform thickness but with optical thickness similar to that of transmission structure 240 can alternatively be produced, for example, with a technique similar to that shown in FIG. 9. Rather than a uniformly varying radiation function with a constant gradient, light source 230 can provide a step-like radiation function, either by scanning or by concurrent radiation. Or light source 230 could provide a constant radiation function through a light absorbing structure with a step-like absorption function.

The techniques illustrated in FIGS. 4-11 could be implemented in various other ways, with different cells of a photosensor array or different positions of a position sensor photosensing slightly different subranges of a range of photon energies. For example, additional details about various production and calibration techniques and characteristics of transmission structures that could be employed are described in co-pending U.S. patent application Ser. No. 10/922,870, entitled "Chip-size Wavelength Detector" and incorporated herein by reference in its entirety.

If quantities photosensed by the cells are read out in parallel and compared, such as in the way suggested in FIG. 2, wavelength shift information about incident photons can be obtained. As illustrated in FIG. 3, nearby cells, such as in a parallel row, can photosense quantities of photons throughout the range of photon energies to provide reference information. If adjacent cells in the array have overlapping subranges, computational techniques such as deconvolution can be used to improve accuracy.

In general, the resolution of a technique as in any of FIGS. 4-11 depends heavily on the number of cells in an array, the full width half maximum (FWHM) of the transmission peak, and the peak shift per cell. The smaller the FWHM and the peak shift, the better the resolution. On the other hand, the totally covered spectral width can be enhanced by increasing the FWHM and the peak shift per cell. Therefore, the technique can be customized to the needs of a specific application. For example, the use of a Fabry-Perot cavity as in FIG. 4 enables very high spectral resolution, while a version with multiple cavities and many layers as in commercially available products will be favorable for applications with low light intensities in combination with small spectral resolution such as with fluorescence. With such an approach, the spectral width of the transmission window and the reflectivity of the stop band can be optimized separately, which may be advantageous because the reflectivity of the stop band determines stray light suppression. It would also be possible to use a single laterally graded distributed Bragg reflector (DBR) mirror as in FIGS. 6 and 7 to obtain a photosensor array with high light sensitivity but limited wavelength resolution, appropriate for fluorescence or luminescence sensing.

A particular advantage of optical stimulus shift sensing as in FIGS. 1 and 2, when implemented with techniques similar to those of FIGS. 3-11, is that laterally varying transmission and reflection properties of the coating over the photosensor array define a correlation between position and photon energy. Therefore the spatially dependent signal from the photosensor array contains information about wavelength shifts due to stimulus change.

In experimental implementations, a coating as in FIG. 4 typically transmits approximately 60% of photons in its respective subrange. The subranges can be chosen with wavelengths that span between 0.01 and tens of nanometers (nm), depending on the design and gradient of the coating and the cell size of the photosensor array. Very high light yield can be achieved by using a highly sensitive photosensor, such as an avalanche photosensor array.

In contrast to transmission structures 160, 180, 210, 220, and 240, any coating or other transmission structure over row 102 in FIG. 3 must function as a gray filter across the range $\lambda_{all}$ in order to provide a suitable reference. It may also be possible to leave row 102 uncoated in some implementations.

Techniques involving optical stimulus change measurement by photosensing in subranges to obtain wavelength shift information, as exemplified by the implementations in FIGS. 1-11, can be implemented in many different ways for a wide variety of applications. For example, photons incident on assembly 34 could be obtained in many different ways, some of which are described below.

FIGS. 12-27 illustrate examples of how output light from a stimulus-wavelength converter can be provided to an assembly such as assembly 34 as described above. Some of the examples include spreading components, as explained in greater detail below. In addition to the steepness of a coating gradient and the length of a photosensor array, light beam geometry plays an important role in resolution of photon energies, also referred to as "wavelength resolution." For optimal performance, the light beam would be perfectly parallel, as could be produced with an appropriate lens system. For many applications, however, absolute wavelength resolution is not very critical, and the optical components are not as important.

The various alternative implementations described below typically do not require optics if the output light from the converter is already parallel, but divergent beams are more typical. Although the examples below are described in terms of output light from optical fiber endings, point-like outputs, broad area sources, or arrays of one of these, the same or similar configurations could be used for output light from integrated optical components such as waveguides, for photonic crystals, for optical biosensors, and so forth. Also, output light from a non-fiber stimulus-wavelength converter could be coupled into one or more optical fibers and transmitted or guided by the fibers to a light sensing assembly. For example, the reflected light from a photonic crystal sensor can be either directly incident on a light sensing component or can be transmitted to a light sensing component via an optical fiber. In a specific example, a photonic crystal can include a dielectric material with a high refractive index that is periodically altered with another material or, for example, air; the spacing of the resulting periodic features within the dielectric material is between approximately 10 nm and 1000 nm.

Figure 12:
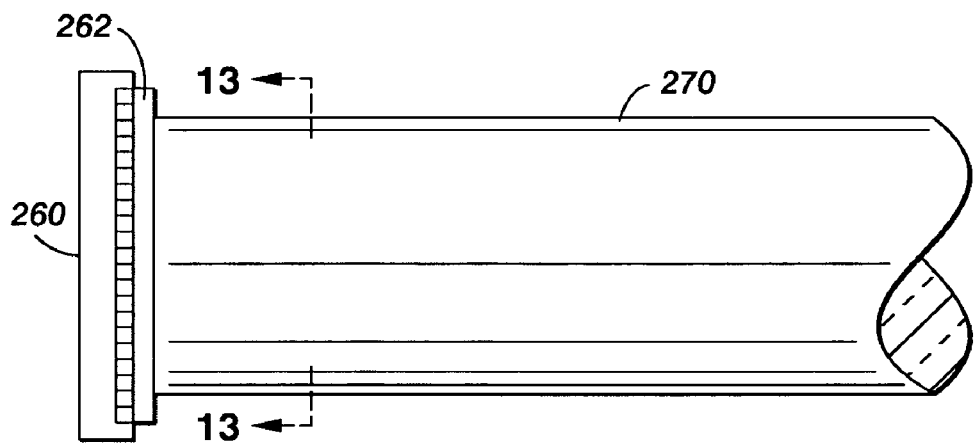
FIG. 12 is a schematic side view of an implementation of a device as in FIG. 1.
Figure 13:
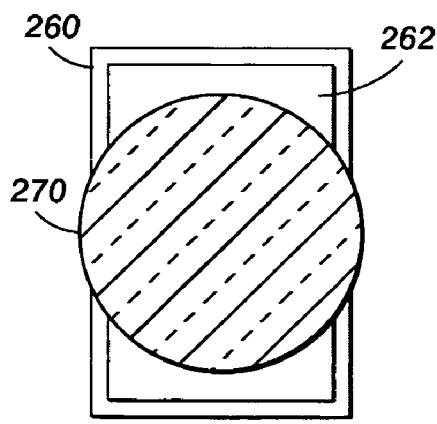
FIG. 13 is a cross-sectional view of the implementation of FIG. 12, taken along the line 13-13.

In FIG. 12, photosensor array 260 is covered by coating 262, a laterally varying transmission structure implemented in any of the ways described above. Fiber 270 provides the light output from a stimulus-wavelength converter of any of the types described above, and could alternatively be any other type of broad area output light source, whether homogeneous or inhomogeneous; if inhomogeneous, quantities photosensed by reference cells can be used to adjust quantities photosensed by subrange cells, as mentioned above in relation to the reference cells in FIG. 3. In any case, the end of fiber 270 is positioned as close as possible to the surface of coating 262. As shown by the cross-sectional view in FIG. 13, fiber 270 can have approximately the same cross-sectional area as the area of array 260, so that light from fiber 270 can be spreaded across approximately the entire surface of coating 262. This configuration provides cheap and simple alignment, but is not suitable for high wavelength resolution. Fiber 270 could be any appropriate fiber, such as a glass or polymer optical fiber. In this configuration, spreading of output light occurs at the interface between fiber 270 and coating 262, because the surface of fiber 270 disposed toward coating 262 functions as a spreading component.

Figure 14:
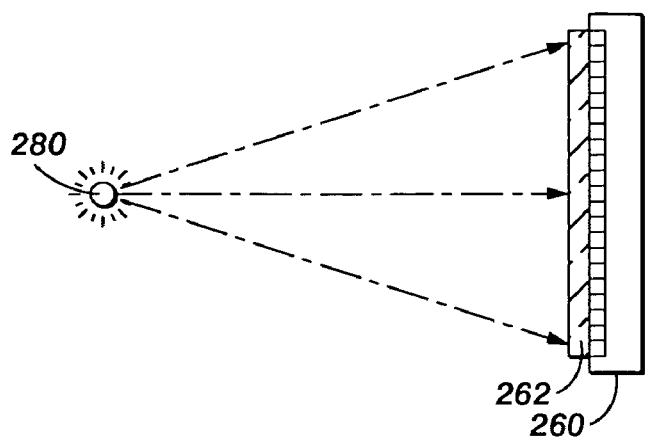
FIG. 14 is a schematic side view of another implementation of a device as in FIG. 1.

In FIG. 14, output light source 280 is a point-like output such as an LED or an optical fiber that provides a divergent output light beam and is positioned a sufficient distance from coating 262 to illuminate the entire sensing area of photosensor array 260. As in the implementation of FIGS. 12 and 13, this implementation allows cheap and simple alignment, but is not suitable for high wavelength resolution. In this configuration, spreading of output light occurs in the distance or gap between source 280 and coating 262, because air, gas, a transparent medium, or vacuum in the gap functions as a spreading component.

Figure 15:
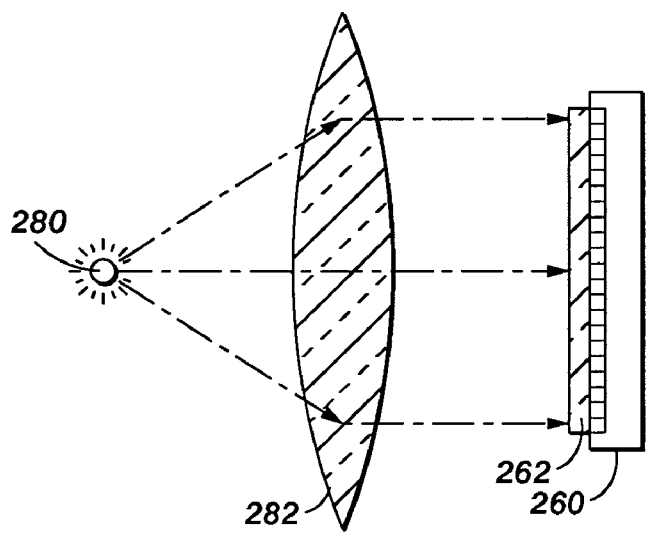
FIG. 15 is a schematic side view of another implementation of a device as in FIG. 1.

In FIG. 15, lens 282 is positioned between output light source 280 and coating 262, making the divergent beam from source 282 parallel. This configuration also allows for a simple alignment, and, in addition, makes it possible to obtain high wavelength resolution. In this configuration, spreading of output light occurs in the distance or gap between source 280 and lens 282, because air, gas, a transparent medium, or vacuum in the gap functions as a spreading component. In an alternative implementation, lens 282 actually images a broad area light source (e.g. a fiber end facet) onto coating 262.

Figure 16:
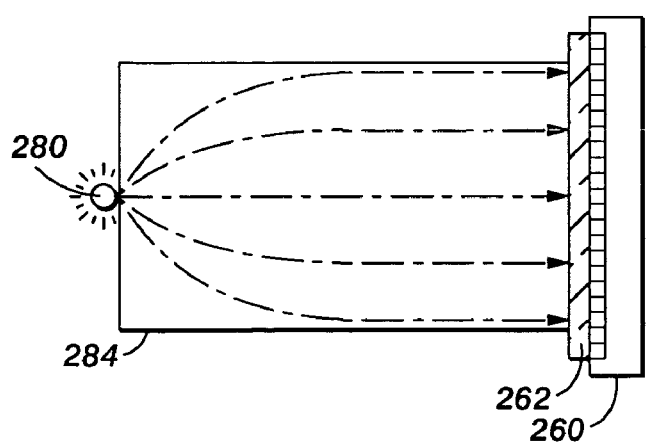
FIG. 16 is a schematic side view of another implementation of a device as in FIG. 1.

In FIG. 16, optical component 284 is positioned between point-like output light source 280 and coating 262, and can be a SELFOC® or gradient index (GRIN) lens that makes the divergent beam from source 280 parallel. This configuration has the same advantages as that of FIG. 15, but the sizes of lenses that can be used in this configuration are limited to those that are available. Additionally, this configuration enables more robust implementations in which all components are attached to each other; this is possible, for example, using a commercially available GRIN lens with its focal point right at its surface. In this configuration, spreading of output light occurs within lens 284 near source 280, because that region of lens 284 functions as a spreading component.

Figure 17:
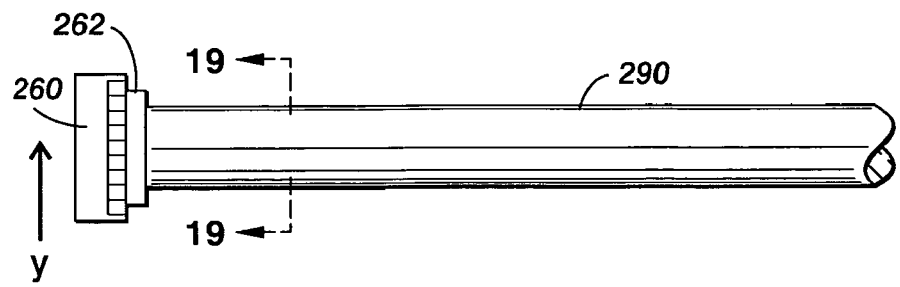
FIG. 17 is a schematic side view of another implementation of a device as in FIG. 1.
Figure 18:
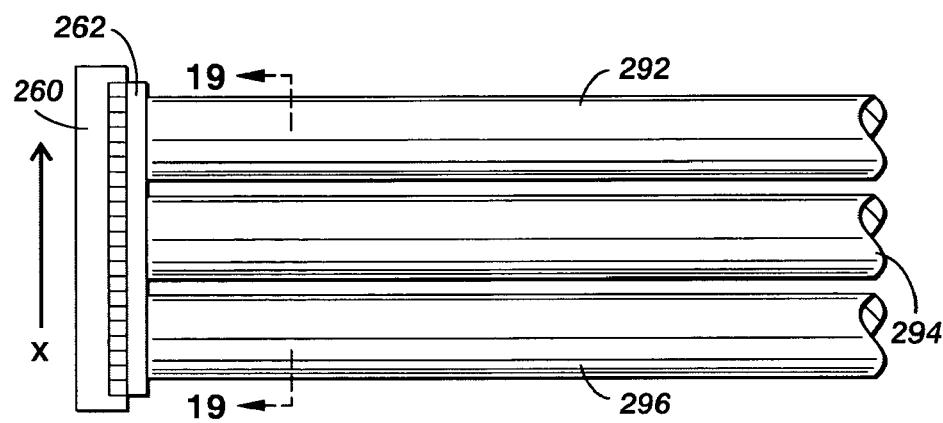
FIG. 18 is a schematic top view of the implementation in FIG. 17.
Figure 19:
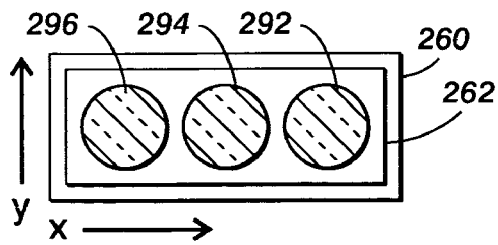
FIG. 19 is a cross-sectional view of the implementation as in FIGS. 17 and 18, taken along the lines 19-19.

FIGS. 17-19 illustrate an implementation similar to FIG. 12, but with a bundle 290 of glass or polymer optical fibers butt-coupled, i.e. positioned with their ends as close to coating 262 as possible. In the illustrated example, bundle 290 includes fibers 292, 294, and 296, and photosensor array 260 can have an optical thickness gradient in the y-direction and a homogeneous coating in the x-direction. This enables sensing of the same photon energy ranges for all fibers; an additional gradient in the x-direction as in FIG. 8 would enable sensing of different photon energy ranges for different fibers. As in FIG. 12, this configuration allows for cheap and simple alignment, but is not suited for high wavelength resolution. In this configuration, spreading of output light occurs at the interfaces between fibers 292, 294, and 296 and coating 262, because the surfaces of fibers 292, 294, and 296 disposed toward coating 262 function as spreading components. Output light sources similar to bundle 290 could also be used in the configurations shown in FIGS. 14-16.

Figure 20:
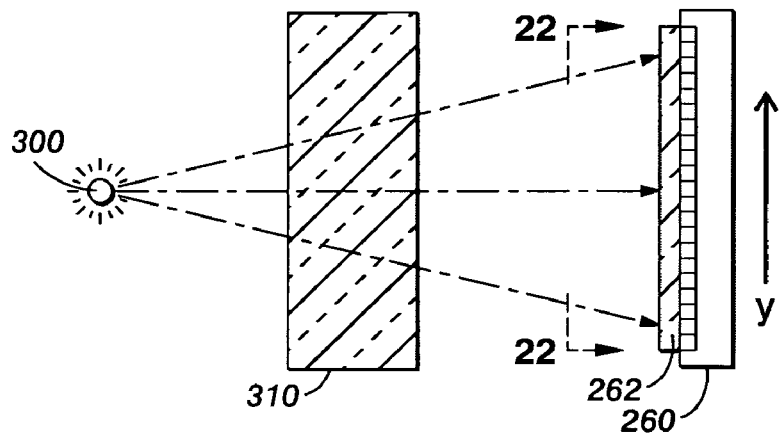
FIG. 20 is a schematic top view of another implementation of a device as in FIG. 1.
Figure 21:
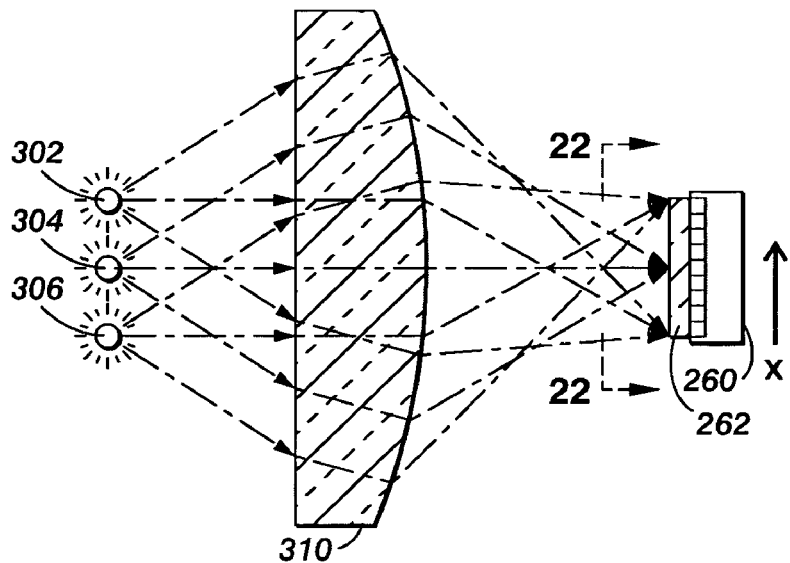
FIG. 21 is a schematic side view of the implementation of FIG. 20.
Figure 22:
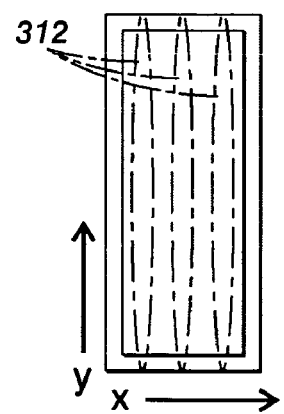
FIG. 22 is a cross-sectional view of the implementation of FIGS. 20 and 21, taken along the lines 22-22.

FIGS. 20-22 illustrate a configuration in which multiple divergent beams are received from different output light sources such as LEDs or optical fibers, positioned at a distance from coating 262 in order to illuminate the entire area of photosensor array 260 in the y-direction. In FIG. 20, the sources are shown from the side, represented by aligned source 300, while in FIG. 21, each individual source is shown separately, as sources 302, 304, and 306. Sources 302, 304, and 306 could each be point-like, or stripe-like LEDs or linear fiber bundles. A configuration similar to that in FIGS. 20-22 could also be used with broad area sources. Sources 302, 304, and 306 can then indicate subareas of the broad area source that can be analyzed independently; for example, subareas can be analyzed to measure photon energy homogeneity over the broad area.

Lens 310 in FIGS. 20 and 21 represents any appropriate positive anamorphic lens or lens group, and is illustratively shown as a piano-convex cylindrical lens. As a result, lens 310 focuses each beam in the x-direction, as shown in FIG. 21, while permitting each beam to continue to spread in the y-direction, as shown in FIG. 20, resulting in multiple spots or stripes 312 as shown in FIG. 22. As in FIG. 15, spreading of output light in the y-direction occurs in the two distances or gaps before and after lens 310, because air, gas, a transparent medium, or vacuum in the gaps functions as a spreading component. If the stripes are adequately resolved in the x-direction, this configuration avoids cross-talk between different output light sources. As in FIGS. 17-19, coating 262 has a gradient in the y-direction, but is homogeneous in the x-direction, but could alternatively be inhomogeneous in the x-direction as discussed above.

Figure 23:
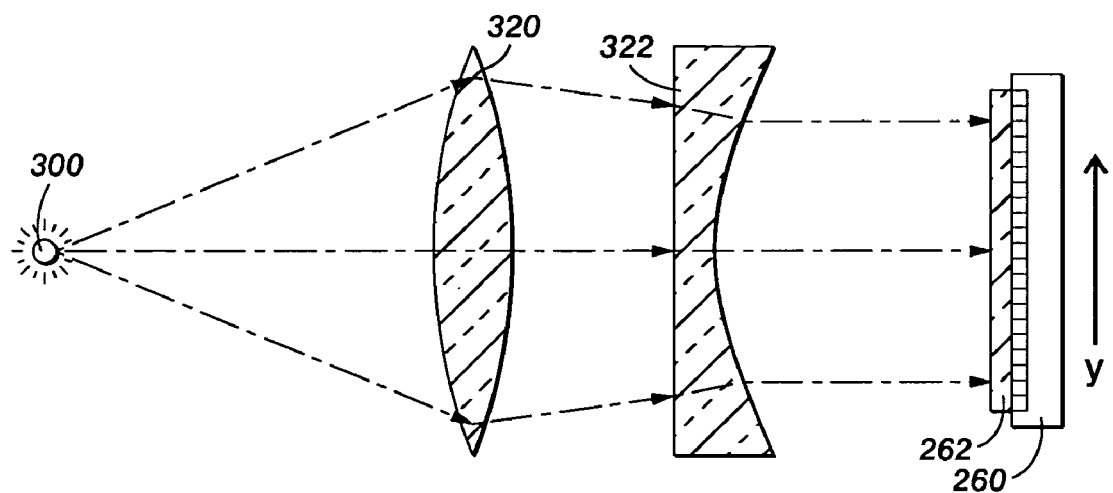
FIG. 23 is a schematic top view of another implementation of the device of FIG. 1.
Figure 24:
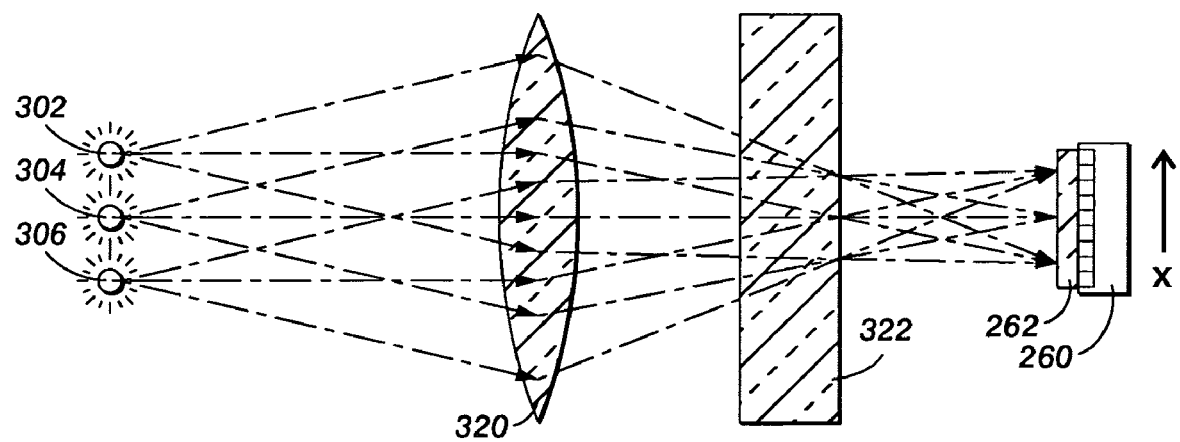
FIG. 24 is a schematic side view of the implementation of FIG. 23.

FIGS. 23 and 24 illustrate another configuration that would produce multiple spots or stripes as illustrated in FIG. 22. In this implementation, the optical components include both imaging lens 320 and any appropriate negative anamorphic lens or lens group, illustratively shown as a piano-concave cylindrical lens 322, while other components are the same as in FIGS. 19-21. The lenses 320 and 322 image the output light beams in the x-direction to avoid cross-talk between beams, but allow each beam to remain spreaded over the whole width of array 260 in the y-direction, due to the effect of lens 322. Due to this special configuration, the light is substantially parallel in the y-direction enabling higher wavelength resolution. In this configuration, spreading of output light occurs in the distance or gap between sources 302, 304, and 306 and lens 320, because air, gas, a transparent medium, or vacuum in the gap functions as a spreading component. A configuration similar to that in FIGS. 23 and 24 could be implemented with a Selfoc® lens array instead of imaging lens 320. Also, a configuration similar to that in FIGS. 23 and 24 could also be used with broad area sources as discussed above.

Figure 25:
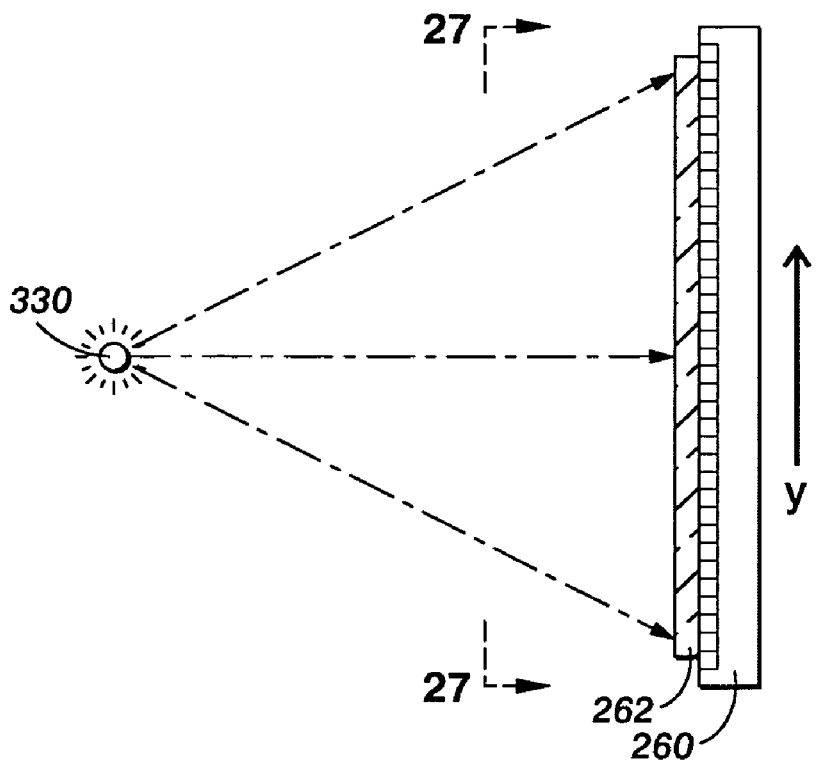
FIG. 25 is a schematic top view of another implementation of the device of FIG. 1.
Figure 26:
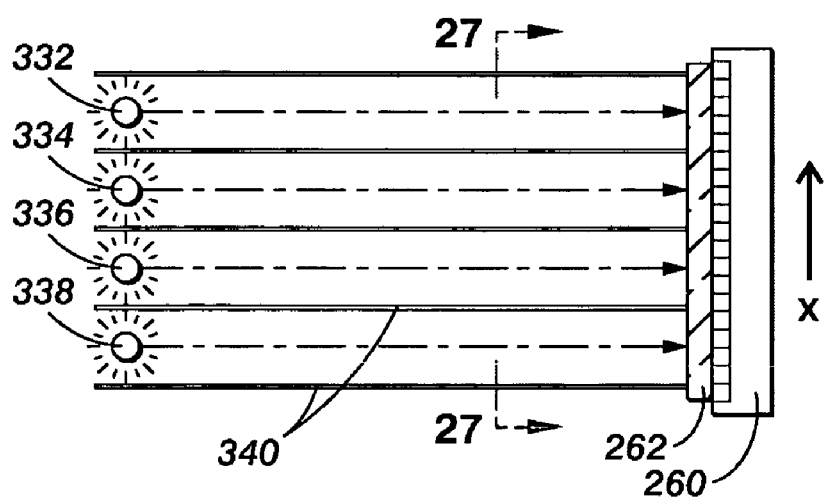
FIG. 26 is a schematic side view of the implementation of FIG. 25.
Figure 27:
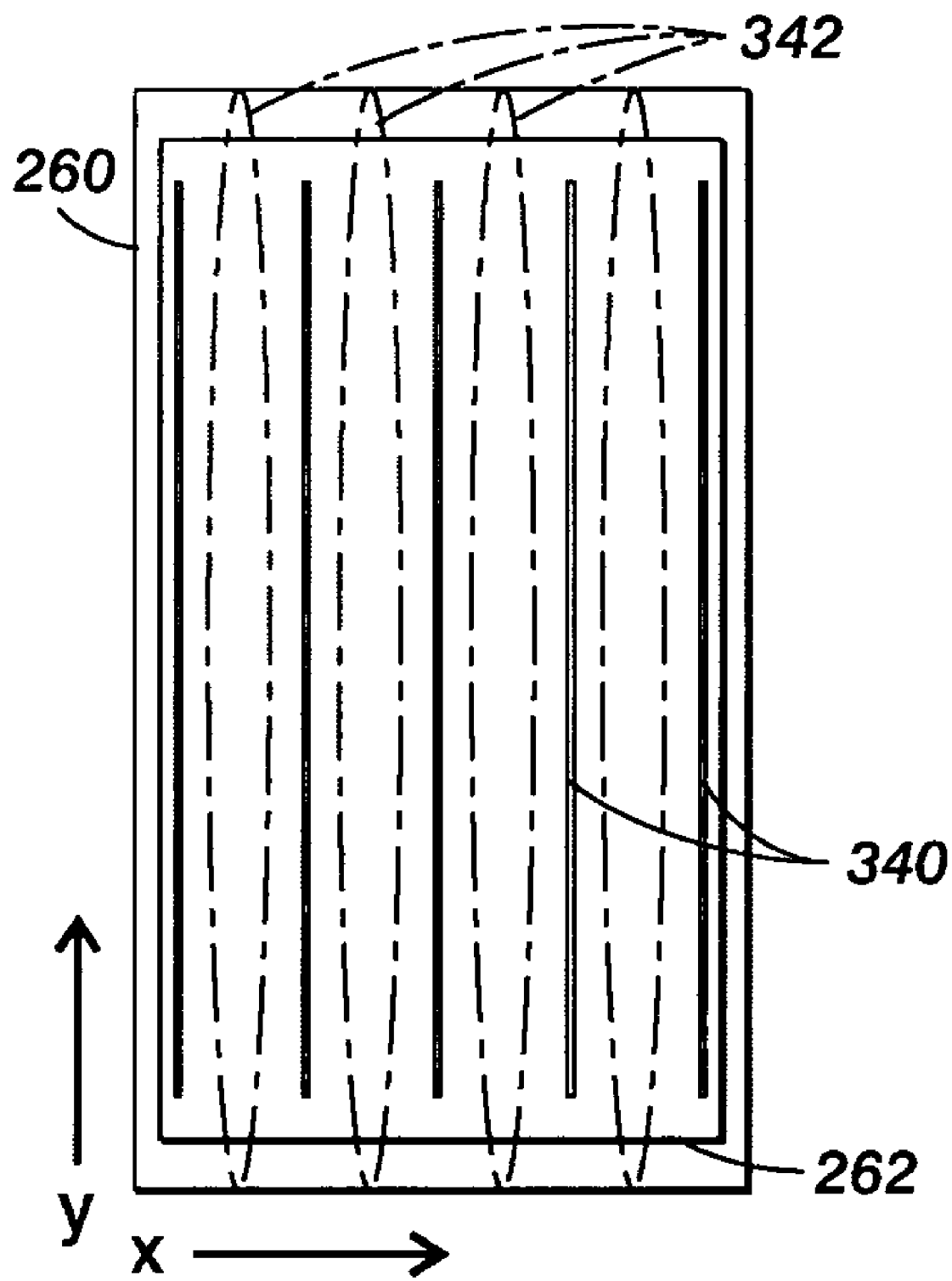
FIG. 27 is a cross-sectional view of the implementation of FIGS. 25 and 26, taken along the lines 27-27.

FIGS. 25-27 illustrate yet another example in which multiple point-like or stripe-like light sources such as LEDs or linear fiber bundles provide output light beams. In the view in FIG. 25, all of the sources are aligned, represented by aligned source 330, while each source 332, 334, 336, and 338 is shown individually in FIG. 26. Rather than lenses or lens-like optical components as in FIGS. 20-24, this configuration includes blades 340, which could be reflecting blades, and which prevent cross-talk between different beams. As a result, a pattern of multiple spots or stripes 342 is produced, as shown in FIG. 27. In this configuration, spreading of output light occurs in the distance or gap between each of sources 332, 334, 336, and 338 and coating 262, because air, gas, a transparent medium, or vacuum in each gap functions as a spreading component. In other respects, this implementation is similar to those of FIGS. 20-24.

Various other techniques could be used to provide output light from a stimulus-wavelength converter to an implementation of assembly 34. The techniques described in relation to FIGS. 12-27 are merely illustrative, and could be varied in many ways.

Figure 28:
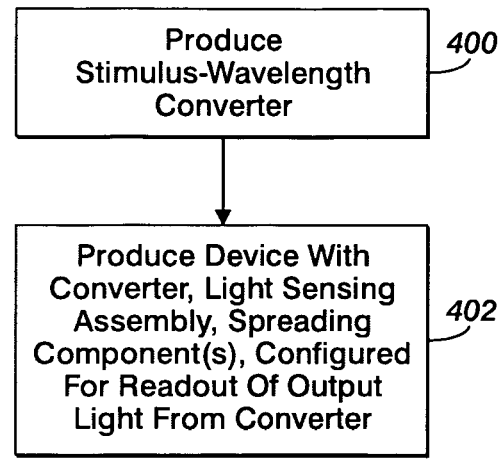
FIG. 28 is a flow chart showing operations performed in producing and using a device as in FIG. 1.

FIG. 28 illustrates exemplary operations in producing apparatus like device 10 in FIG. 1. In particular, the operations in FIG. 28 make it possible to produce a device in which output light from a stimulus-wavelength converter is incident on readout components that include a light sensing assembly and one or more spreading components.

The operation in box 400 in FIG. 28 produces a stimulus-wavelength converter of any of the types described above. For example, the operation in box 400 could produce a fiber-optic sensor with FBGs, a POF sensor, a photonic crystal sensor, an optical biosensor, etc.

The operation in box 402 then produces a device with the converter from box 400, a light sensing assembly, and one or more spreading components, configured so that output light from the converter is incident on the light sensing assembly, such as in one of the ways described above in relation to FIGS. 12-27. This operation can be performed in any appropriate way, including butt-coupling as in FIGS. 12, 17, and 18 or with spaced components as in FIGS. 14, 15, 20, 21, and 23-26.

Figure 29:
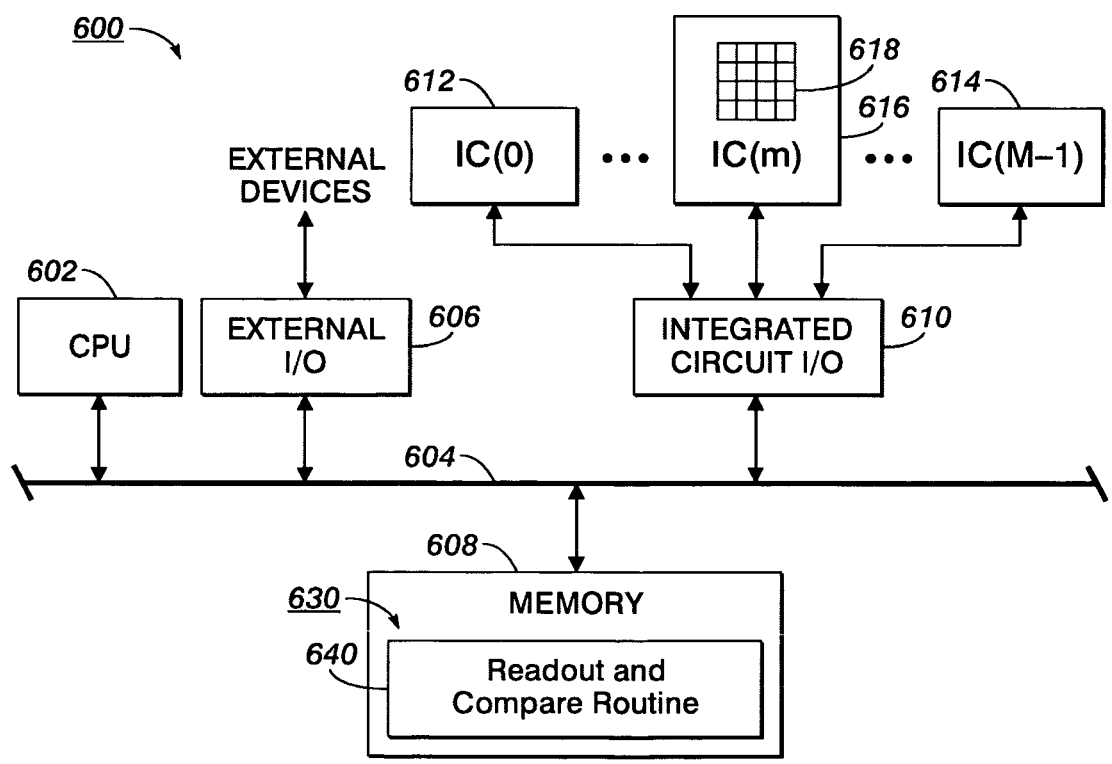
FIG. 29 is a schematic block diagram of a system that could control a number of devices as in FIG. 1.

FIG. 29 illustrates features of a system that includes one or more devices as in FIG. 1. In FIG. 29, system 600 is an exemplary system that could be used to obtain wavelength information from light output from stimulus-wavelength converters as described above. System 600 illustratively includes central processing unit (CPU) 602 connected to various components through bus 604, but a wide variety of other architectures could be employed, including any appropriate combination of hardware and software, as well as specialized hardware components such as application specific integrated circuits (ASICs) for one or more of the illustrated components or in place of a software component executed by CPU 602.

System 600 also includes external input/output (I/O) component 606 and memory 608, both connected to bus 604. External I/O 606 permits CPU 602 to communicate with devices outside of system 600. For interactive applications, external I/O 606 could be connected to a suitable user interface, such as a monitor and keyboard (not shown). Additional components connected to bus 604 are within or connected to system 600. In the illustrated implementation of system 600, IC I/O 610 is a component that permits CPU 602 to communicate with one or more ICs in sensing assembly 22. M ICs are illustrated by a series from IC(0) 612 to IC(M−1) 614, including IC(m) 616 with a photosensor array 618.

Memory 608 illustratively includes program memory 630, although instructions for execution by CPU 602 could be provided in any of the ways described above. The routines stored in program memory 630 illustratively include readout and compare routine 640. In addition, program memory 630 could store various additional subroutines (not shown) that CPU 602 could call in executing routine 640.

In executing routine 640, CPU 602 can provide signals to each of ICs 612 through 614 to read out subrange cells and to compare the photosensed quantities to obtain wavelength information such as differential quantities. Before comparison, routine 640 can also optionally read out reference cells and use their photosensed quantities to adjust photosensed quantities from subrange cells, such as with techniques described in co-pending U.S. patent application Ser. No. 11/316,438, entitled "Photosensing Throughout Energy Range and in Subranges" and incorporated herein by reference.

Routine 640 can perform comparison in several ways, depending on the type of wavelength information being obtained. To obtain wavelength shift information, photosensed quantities from two cells or two sets of cells can be compared similarly to the technique illustrated in FIG. 2; with appropriate differential amplifier circuitry on an IC, routine 640 may be able to perform the comparison with especially high resolution by controlling readout from the cells to the differential amplifier, after which the analog comparison result can be converted to a digital value for transfer through bus 604 to CPU 602. A differential amplifier can also be used for an especially high resolution comparison of intensities of two different currents of a position sensor. Rather than a differential amplifier, any other suitable analog component could be used that provides a biased or unbiased analog difference or analog ratio.

Photosensed quantities could instead be digitized before comparison, in which case CPU 602 could perform any appropriate routine to obtain a digital differential quantity or any other data indicating a comparison result. Such a routine could also include normalizing or otherwise adjusting each digitized value prior to comparison. The routine could perform subtraction, division, or any other operation that produces a result indicating the difference between two photosensed quantities.

Although digital comparison is not likely to be as precise as high resolution analog comparison, it may allow greater flexibility. For example, rather than simply performing pairwise comparison, CPU 602 could divide all the non-zero or above-threshold photosensed quantities into two groups in any appropriate way, add the quantities to obtain a summed quantity for each group, and then compare the summed quantities, possibly after weighting for difference in the number in each group. The groups could be chosen based on position or any other suitable criterion.

More generally, to increase resolution, CPU 602 can compare photosensed quantities with calibration values. The term "calibration value" is used herein to refer to any value obtained by a measurement that either establishes a standard or is based on a previously established standard. A calibration value could, for example, indicate how to categorize, weight, or otherwise interpret, adjust, or correct a given measured value such as a photosensed quantity or photosensed position. Once obtained, a calibration value is typically saved in an appropriate form for subsequent comparison with measured values. Where a calibration value indicates a quantity of photons, it may be referred to as a "calibration quantity".

Absolute wavelength resolution is important to quantify the absolute value of a stimulus (e.g. the actual temperature), while relative wavelength resolution is important to quantify the change in a stimulus (e.g. the size of a temperature change). Both types of information require calibration to obtain calibration values for later comparison. It should be noted, however, that absolute wavelength calibration can change more easily than relative wavelength calibration as a result of small changes in the setup (e.g. non-collimated light input), so that relative wavelength resolution is more robust.

During calibration, the readout components are illuminated with a known light source and the response is stored in an appropriate calibration data structure. Exemplary calibration techniques are described in co-pending U.S. patent application Ser. No. 10/922,870, entitled "Chip-size Wavelength Detector" and incorporated herein by reference in its entirety.

For absolute wavelength information, a calibration data structure can indicate correspondences between positions and wavelengths; for relative wavelength information, a calibration data structure can indicate correspondences between position differences or relative photosensed quantities, on the one hand, and wavelength, peak value, distribution, or stimulus value differences on the other. Routine 640 can compare quantities it reads out with one or more calibration data structures to obtain either or both of these types of information.

Wavelength information obtained by routine 640 can be combined in an appropriate data structure (not shown), such as by forming a data array or list. After wavelength information has been obtained, CPU 602 can use the raw wavelength information, for example, to calculate or obtain from a calibration data structure a corresponding value for the stimulus or for a stimulus change (e.g. temperature, pressure, presence or absence of analyte, etc.). CPU 602 can provide the wavelength information or corresponding values through external I/O 606. For example, all of the wavelength information or corresponding values could be combined into a single data structure and provided through external I/O 606 through a suitable streaming operation.

In general, system 600 could be implemented with any devices that include stimulus-wavelength converters. Furthermore, system 600 could be implemented for many applications, some of which are illustrated below.

Figure 30:
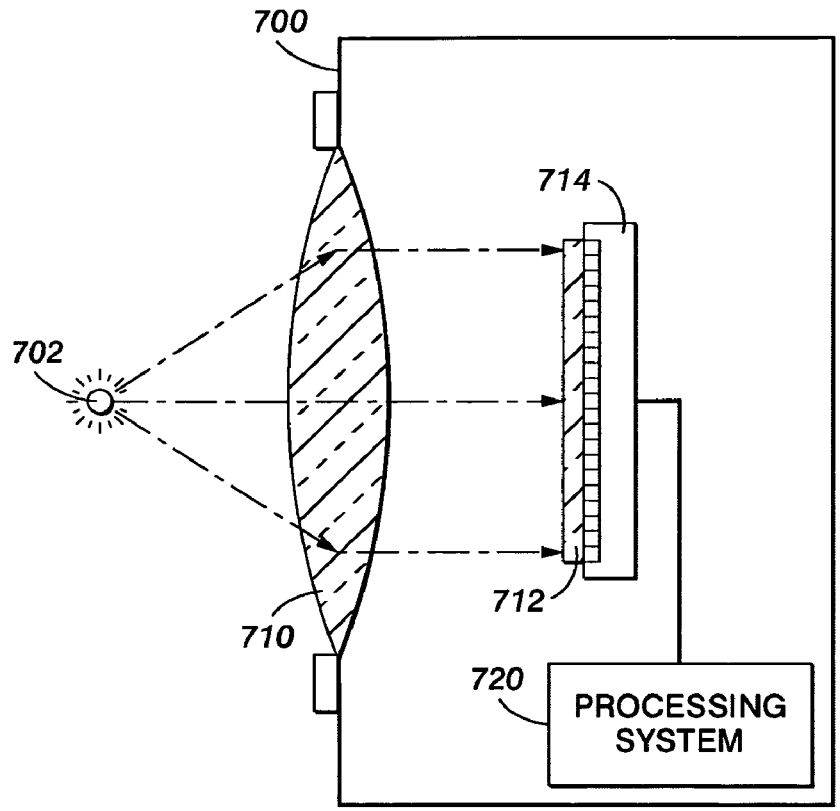
FIG. 30 is a schematic diagram of a camera that includes one or more devices as in FIG. 1.

FIG. 30 shows camera 700, an example of apparatus that includes one or more devices as in FIG. 1. Camera 700 receives output light from a stimulus-wavelength converter, represented in FIG. 30 by point-like source 702.

Output light from source 702 is spreaded as it propagates across the gap to imaging lens 710, and then is directed in a collimated fashion onto an assembly that includes a laterally varying transmission structure such as coating 712 and also a photosensor component such as IC 714. Collimation can avoid error arising if coating 712 were laterally inhomogeneous due to dependence on incidence angle at its entry surface. Processing system 720 then obtains readout signals from IC 714 and uses the readout signals to obtain wavelength information.

A camera with general features as shown in FIG. 30 has been implemented by modifying an inexpensive commercially available Webcam-type camera with a cylindrical lens and a CCD array. A linear variable filter was placed over the CCD array, such as a GaAs/AlAs graded Fabry-Perot cavity produced similarly to the technique in FIG. 8 or a commercially available filter available from JDS Uniphase. The camera was then positioned to receive light from a wavelength tunable light source, such as a tunable VCSEL from ULM-Photonics, which was controlled to provide spots of light at several different wavelengths including 942.81 nm, 943.08 nm, 943.45 nm, 943.92 nm, 944.55 nm, and 945.37 nm. For each wavelength, signals read out from the array were converted into an image in the conventional manner, from which positions of maximum photon quantity could be visually obtained.

Figure 31:
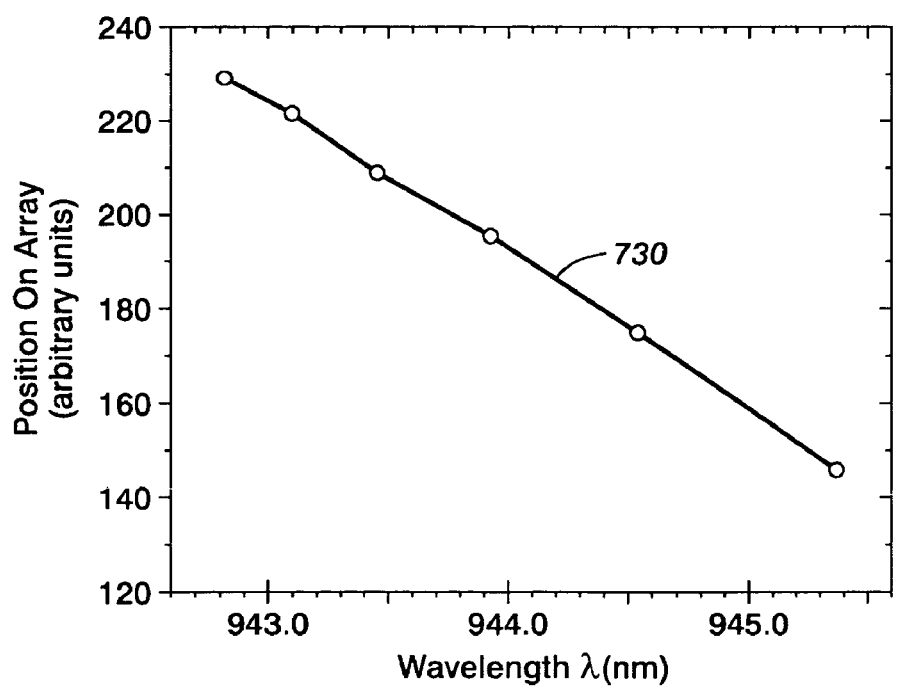
FIG. 31 is a graph showing results obtained from an implementation of the camera in FIG. 30.

FIG. 31 summarizes the positions obtained visually as described above for the wavelengths listed above, with the horizontal axis representing wavelength in nm and with the vertical axis representing position on the array in arbitrary units, specifically numbers of cells in the array. For each wavelength, the position value was visually obtained, and curve 730 connects the position values of spots for the above-listed wavelengths. As can be seen, wavelengths were successfully resolved that differed by less than 0.1 nm.

Figure 32:
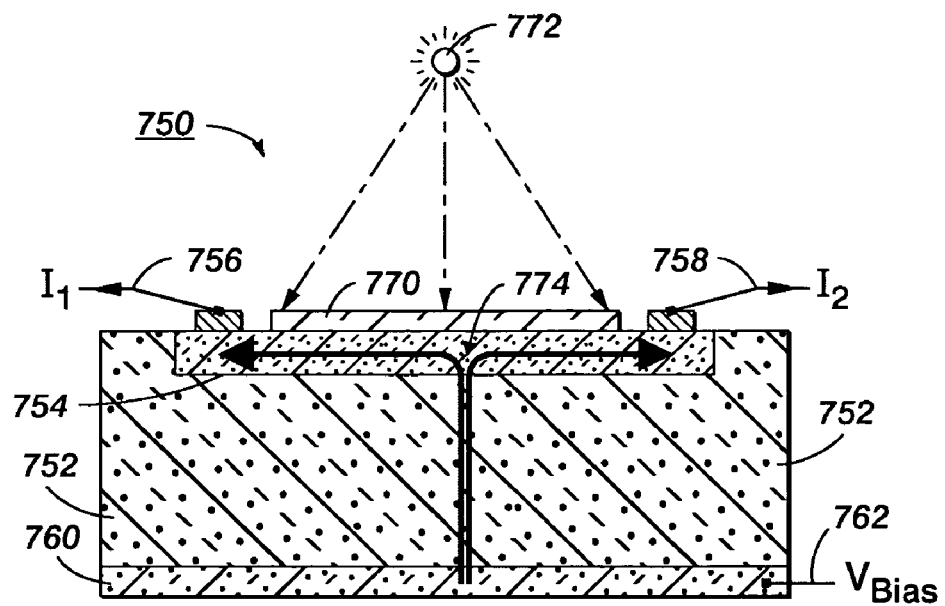
FIG. 32 is a schematic side view of a test implementation of a device as in FIG. 1 with an assembly that includes a position sensor.

FIG. 32 shows a test implementation similar to techniques described in co-pending U.S. patent application Ser. No. 10/922,870, entitled "Chip-size Wavelength Detector" and incorporated herein by reference in its entirety. Device 750 includes a three-terminal semiconductor position sensor that responds to an incident light spot by providing a signal indicating the light spot's position on the upper surface of the sensor. The sensor includes n-type silicon substrate 752 with two resistive layers separated by a p-n junction. On the upper side is an ion implanted p-type resistive layer 754 with two contacts or electrodes 756 and 758 at opposite ends. On the lower side is an ion implanted n-type resistive layer 760, serving as the device's bias electrode 762.

Over the upper surface of substrate 752 is laterally varying transmission structure 770, which can be implemented in any of the ways described above in relation to FIGS. 4-11 but has been experimentally implemented with a structure like that in FIG. 4, designed to transmit wavelengths in part of the spectral range where silicon photon detectors are sensitive. When light source 772 illuminates structure 770 with a single wavelength within this spectral range at which structure 770 is transmissive, structure 770 provides a spot at the wavelength's corresponding position 774 to the upper surface of substrate 752, and photocurrent flows from point 774 through resistive layers 754 and 760 to electrodes 756 and 758. The currents from electrodes 756 and 758 can be provided to a differential amplifier as described above or converted to digital values and compared to obtain a signal indicating the location of position 774.

Any other suitable spreading, separating, and propagation techniques could be used in the setups shown in FIGS. 30 and 32, including any of those described above in relation to FIGS. 12-27. Position sensors like that shown in FIG. 32 and other position sensor arrays and devices in general can be used with any of the techniques in FIGS. 12-27.

Figure 33:
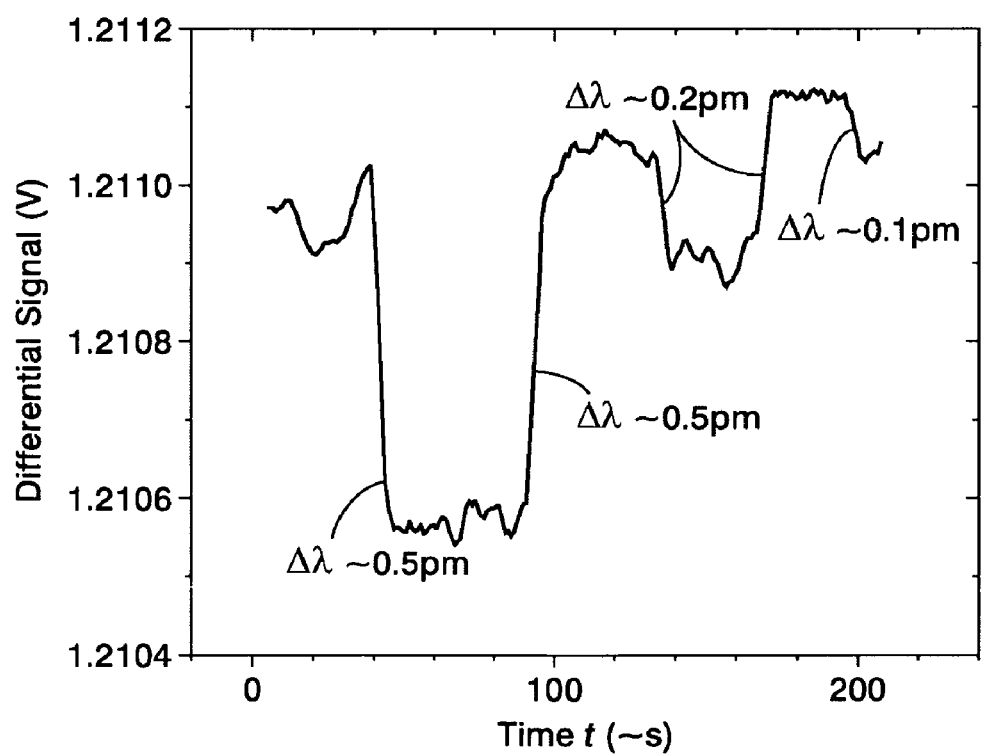
FIG. 33 is a graph showing response to change in wavelength for the test implementation of FIG. 32.

The graph in FIG. 33 shows that the test implementation in FIG. 32 can perform extremely high, sub-picometer wavelength resolution. In this implementation, light source 772 was a tunable 950 nm VCSEL. The differential signal across electrodes 756 and 758 is shown as a function of time during a session in which the illumination wavelength of the VCSEL was adjusted by increments and decrements (Δλ) of approximately 0.1, 0.2, and 0.5 pm. Each increment and decrement produced a detectable nearly instantaneous excursion of the differential signal, appearing in FIG. 33 as nearly vertical segments of the curve.

Figure 34:
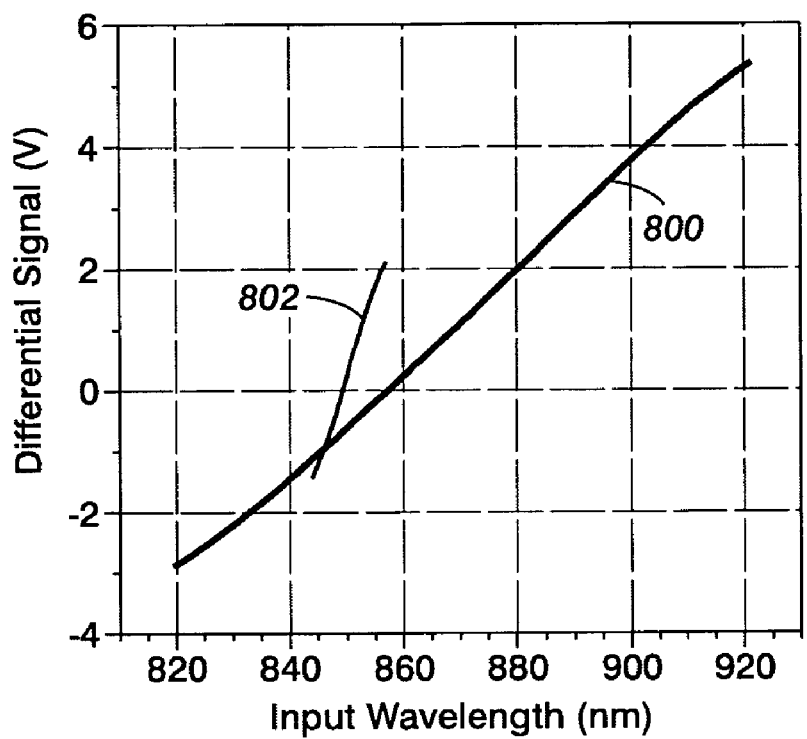
FIG. 34 is a graph showing differential signal as a function of input wavelength for another version of the test implementation of FIG. 32.

The graph in FIG. 34 was obtained with a modified version of the test implementation in FIG. 32. In this version, light source 772 was a spectrally filtered halogen lamp that provides monochromatic light with FWHM of about 1 nm, and with the capability of sweeping the wavelength over a large wavelength range. For curve 800, structure 770 had a wavelength-to-distance gradient of 32 nm/mm, and for curve 802, a gradient of 4 nm/mm. In curve 800, the differential signal changes monotonically over a range of 100 nm with a slope of approximately 86 mV/nm. In curve 802, the differential signal changes similarly, but with a much greater slope. This illustrates an example in which decreasing the gradient improves wavelength resolution but sacrifices wavelength range, while increasing the gradient enables large wavelength range coverage at a lower wavelength resolution.

Figure 35:
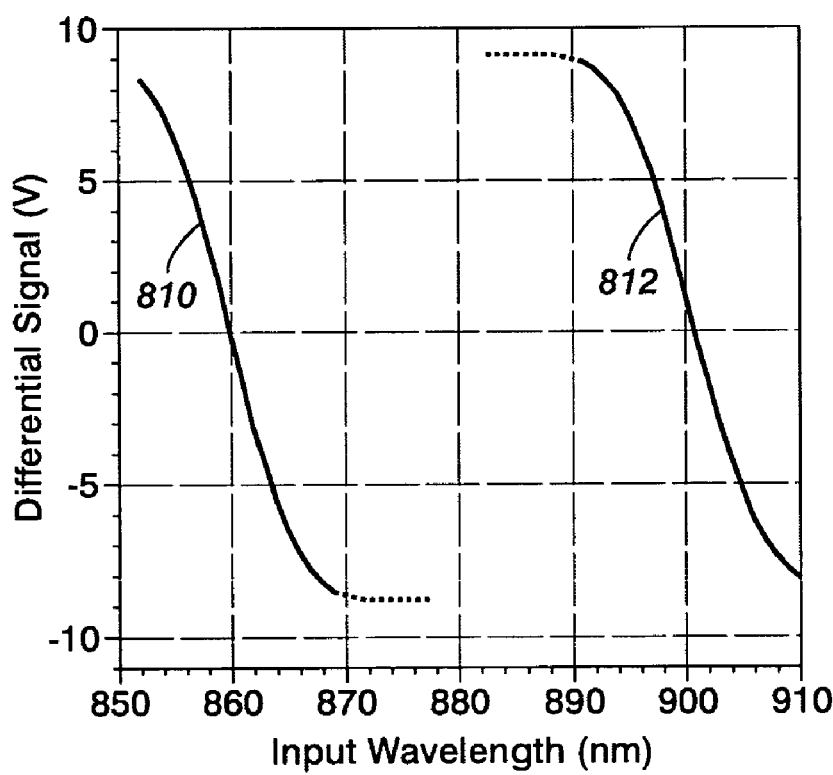
FIG. 35 is a graph showing differential signal as a function of wavelength for a test implementation with an assembly that includes cells as in FIG. 3.

The graph in FIG. 35 was obtained by modifying the setup for FIG. 34, replacing the position sensor with a photosensor array and connecting three consecutive cells in a row of the array to two differential amplifiers, with one differential amplifier comparing the first and second cells and with the other comparing the second and third cells. Curve 810 results from comparing the first and second cells, and curve 812 from comparing the second and third cells. In both curves, the differential signal changes with wavelength, but the two pairs of cells address different wavelength ranges.

Figure 36:
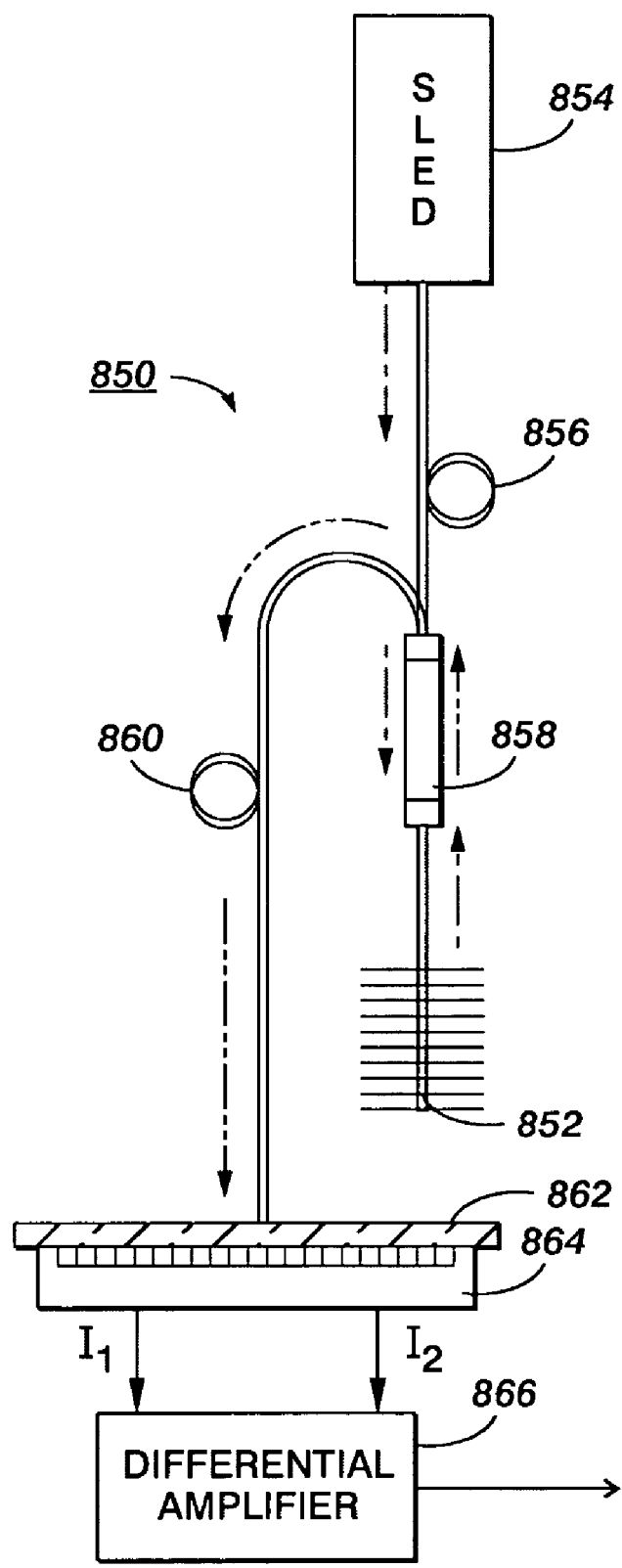
FIG. 36 is a schematic diagram of a test implementation in which a device like that in FIG. 1 was implemented to measure temperature.

FIG. 36 shows another test implementation in a temperature sensing device 850. Device 850 includes FBG sensor 852, an 834 nm FBG mounted at one side on a cooling/heating element that is connected to a temperature controller such that temperature can be tuned by adjusting a heating/cooling current; the other side of sensor 852 was, however, exposed to ambient air, so that temperature control was imperfect. Light source 854 is a super luminescent emitting diode (SLED) that provides light in a narrow band around 817 nm to sensor 852 through fiber 856 and coupler 858, which can be a commercially available 3 dB 2×1 coupler.

Reflected light from sensor 852, with its wavelength indicating information about temperature, returns through coupler 858 and fiber 860 to laterally variable transmission structure 862, implemented in one of the ways described above in relation to FIGS. 4-11 and having a gradient of 32 nm/mm. A spot of light corresponding to the reflected wavelength is provided to photodiode array 864. Two cells of array 864 are positioned to receive two wavelength subranges, and their output currents $I_1$ and $I_2$ are provided to differential amplifier 866 for comparison.

The differential signal from amplifier 866 has a magnitude indicating the reflected wavelength from sensor 852, as shown in FIG. 37. Curve 880 indicates the resistance of a temperature monitoring thermistor integrated into the cooling/heating element as a function of time during a session, where the controller changes the temperature of the cooling/heating element from one to another set value. Curve 882 indicates the differential signal from amplifier 866 as a function of time during the same session. As can be seen, curve 882 follows curve 880 in general and especially during transients. The differences during steady state might result from the effect of ambient air on sensor 852, providing noise that caused its temperature to fluctuate when the resistance was relatively stable.

FIG. 38 shows steady state differential signal as a function of temperature for device 750 in FIG. 36, with the circles indicating measurements for temperatures across a wide temperature range. As can be seen, a linear fit produces the curve y=229-12.2x, so that the sensitivity is approximately 12.2 mV/° C. This sensitivity allows temperature resolution down to 0.1° C.

Figure 39:
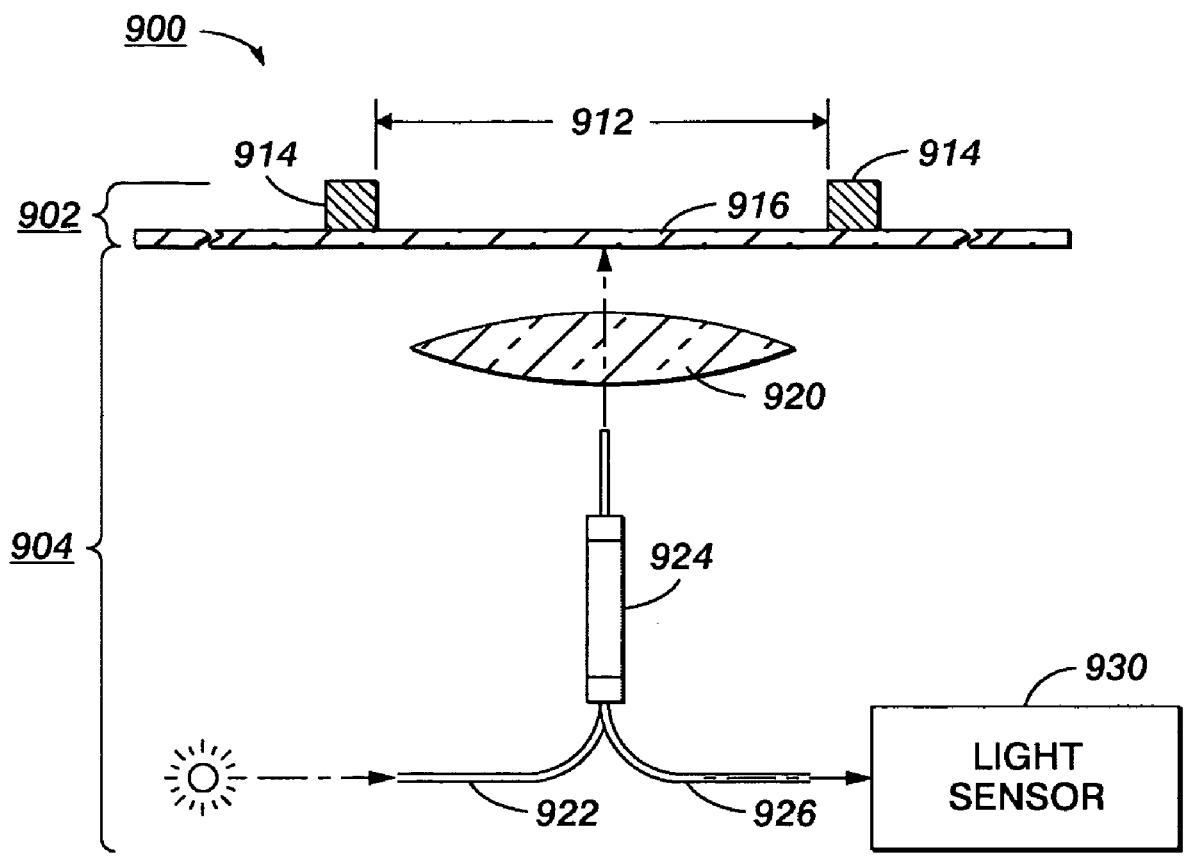
FIG. 39 is a schematic side view of an implementation of a device like that in FIG. 1 to obtain information from a well plate.

FIG. 39 shows device 900, which includes 96-well plate 902 and readout components 904. FIG. 39 shows only parts of well plate 902 and readout components 904, with features relating to one well. Well plate 902 can be used, for example, with equipment that injects a sample of fluid into each well for analysis.

Well plate 902 can be implemented with a BIND Biosensor™ from SRU Biosystems, Woburn, Mass., which functions as an 8×12 array of stimulus-wavelength sensors. In other words, each well 912 is surrounded by walls 914 that function to separate contents of wells and prevent contamination, and walls 914 together form a stable lattice-like framework or structure on one side of which foil grating 916 is mounted. The fluid or other contents of well 912 modify the reflected wavelength of the well's region of grating 916. The well's region of grating 916 therefore includes a "grating component", meaning an optical sensor or optical sensing component that, when illuminated with collimated broadband light, is designed to reflect only a narrow band of wavelengths that depends on the fluid or other contents of well 912. Additional features of well plate 902 are described in U.S. Patent Application Publication Nos. 2003/0077660 and 2004/0223881 and in Cunningham et al., *Journal of Biomolecular Screening*, 9(6), 2004, p. 481, all of which are incorporated herein by reference.

Readout components 904 for each well include collimating lens 920, which receives broadband light through illuminating fiber 922, contained in optical fiber probe 924 with readout fiber 926; each well could be measured by more than one probe 924. Readout fiber 926 transmits reflected light from a well's region of foil grating 916 to light sensor assembly 930, which can be implemented in any of the ways described above. Readout components 904 can include similar components for each well in the array, and a single light sensor assembly 930 can receive reflected output light in parallel from a fiber bundle that includes the readout fibers 926 for an 8-well row of the array or possibly even a two-dimensional fiber array that covers all 96 wells.

Spreading components and other propagation components for the fiber bundle can be configured in one of the ways described above or as described in U.S. Patent Application Publication Nos. 2003/0077660 and 2004/0223881. All the light sensor assemblies 930 for the array can be connected in parallel to circuitry for obtaining wavelength information as described above.

In general, any of the lenses described in relation to FIGS. 1-39 can be implemented or replaced by any suitable type of refractive or diffractive optics, including but not limited to spherical lenses, Selfoc® lenses, and gradient index (GRIN) lenses. Also, any lens described in these examples might be replaced by a lens with similar functionality, e.g. a plano-concave lens might be replaced by a bi-concave lens or any other appropriate negative anamorphic lens or lens group, a plano-convex lens might be replaced by a biconcave lens or any other appropriate positive anamorphic lens or lens group, and so forth.

Some of the implementations of FIGS. 1-39 illustrate examples of apparatus that include a stimulus-wavelength converter, a transmission structure, and a spreading component. The stimulus-wavelength converter provides output light in response to one or more stimuli. The transmission structure has an entry surface at which it receives the output light and an exit surface; the entry surface extends in a first direction and the transmission structure's energy transmission function varies laterally in the first direction. The spreading component spreads the output light from the converter across the entry surface in at least a spreading direction that is not perpendicular to the first direction.

In specific implementations, the converter can provide the output light within a range of photon energies; in response to spreaded light with energies in a given subrange, the transmission structure can provide output photons at a respective position of the exit surface. Also, the converter can provide output light from a fiber end facet, from a point-like source, or from a broad area source. The converter can include a set of optical fibers that each respond to a respective stimulus and provide output light to the spreading component. The spreading direction can be approximately the same as the first direction.

Also, in specific implementations, at least one of the optical fibers can provide light output through an end positioned in a butting relationship adjacent the entry surface, and the spreading component can include a surface at the end. At least one of the fibers can provide light output through an end, and the spreading component can be positioned between the end and the entry surface, such as air, gas, a transparent medium, or vacuum in a gap or part of a Selfoc® or GRIN lens. With two or more optical fibers, the system can also include a separation component that keeps light output from the fibers separate, such as a lens that collimates, images, or focuses or blades. If the fiber ends are aligned in a second direction perpendicular to the first direction, the spreading direction can be approximately the same as the first direction.

In further specific implementations, the apparatus can also include photosensing components that photosense output photons from the exit surface at a set of positions along the first direction. Where the output light includes wavelength information, a system that includes the apparatus can also include circuitry that responds to the photosensing components, providing signals indicating the wavelength information; the circuitry can include a processor.

Implementations in FIGS. 1-39 further illustrate examples of a sensing method that includes receiving output light from a stimulus-wavelength converter that provides the output light in response to one or more stimuli. The method spreads the output light in at least a spreading direction across a transmission structure's entry surface. In response to the spreaded light, the method provides output photons at the exit surface in accordance with an energy transmission function that varies laterally in a first direction in which the entry surface extends. The first direction and the spreading direction are not perpendicular to each other.

In specific implementations, the output light is provided as described above. The method can also, with one or more photosensing components, photosense the output photons at a set of positions along the first direction. If the output light from the converter includes wavelength information, signals indicating the wavelength information can be provided in response to photosensing results.

Some of the implementations in FIGS. 1-39 also illustrate examples of apparatus that includes two or more sources that provide light, a transmission structure as described above, and a propagation component. The propagation component spreads light from each source across the transmission structure's entry surface and keeps the light from the sources separate. The propagation component spreads the light in at least a spreading direction that is not perpendicular to the first direction of the transmission structure.

In specific implementations, the fiber ends are aligned in a second direction approximately perpendicular to the first direction, and the spreading direction can be approximately the same as the first direction. The apparatus can also include one or more stimulus-wavelength converters that provide output light through the sources. Each of the sources can be a fiber end facet, a point-like source, or a broad area source. Each can be an optical fiber end positioned in a butting relationship adjacent the entry surface, and the propagation component can include an optical fiber surface at each end. The propagation component can be positioned between the sources and the entry surface, such as air, gas, a transparent medium, or vacuum in a gap; one or more lenses; or a set of blades.

In general, many additional techniques could be employed in the implementations of FIGS. 1-39, such as adjusting photosensed quantities from subrange cells based on photosensed quantities from reference cells, as described in greater detail in co-pending U.S. patent application Ser. No. 11/316,438, entitled "Photosensing Throughout Energy Range and in Subranges" and incorporated herein by reference. This adjustment could be performed on analog quantities or, after conversion to digital values, on digital quantities.

The implementations in FIGS. 1-39 illustrate various applications of techniques as described above, including readout from stimulus-wavelength converters and other optical sensors; use in a camera or other imaging device; use in temperature measurement; and use in readout of a well plate. Sensing techniques involving laterally varying transmission of light as a function of photon energy, as exemplified by the implementations in FIGS. 1-39, can also be applied in many other applications. A particularly interesting application of optical sensor readout is in automobiles, where optical sensor robustness against EMI is especially valuable. Other applications involve biological, chemical, and environmental sensors.

Various of the techniques described above have been successfully implemented or simulated, including the production of a detector that includes a commercially available IC covered with a laterally graded Fabry-Perot cavity filter on a glass slide. Wavelength resolution has been experimentally determined and successfully simulated on a computer. Anti-resonant waveguide techniques have been successfully tested. As described above, temperature measurement has been successfully performed by using a commercially available detector coated with a laterally varying Fabry-Perot coating.

The exemplary implementations described above are advantageous because they can provide compact, inexpensive components to perform functions such as readout of stimulus-wavelength converters or other optical sensors. In general, the techniques can be implemented in existing sensors, photosensors, and cameras, including camcorders, digicams, and webcams available in the consumer market. The results of photosensing can be read out and compared rapidly.

Readout implementations as described above can be applied in various applications, several of which are described or mentioned above. Readout implementations as described above can also be applied in smart sensors, in sensors with bus capabilities, and in sensors with self-diagnostic capabilities, with self-calibration, and with self-adaptation.

The exemplary implementations described above generally rely on transmission structures that include highly reflective interfaces, so that much of the incident light is reflected and only a small fraction reaches the photosensor array. Therefore, the techniques described above are especially useful in applications in which light intensity is very high or a light source emits through a large area or over an extended time. In addition, the above techniques make it possible to increase sensitivity by choosing very long integration times (without loss of throughput capacity), simpler optics, and no dispersion element. By contrast, some conventional systems such as monochromators lose all light defracted into the $0^{th}$, $2^{nd}$, and higher orders. In the implementations described above, very high light yield can be achieved by combining a transmission structure with a highly sensitive photosensor array, such as one that includes avalanche photodetectors.

In addition, components could have various shapes, dimensions, or other numerical or qualitative characteristics other than those illustrated and described above. For example, in the exemplary implementations described above, cells of a photosensor array photosense in different subranges of an application's photon energy range. The subranges of cells could have any appropriate widths and relationships, and could, for example, overlap or be distinct. The width of a cell's subrange can be chosen by designing the transmission structure and the cell sensing area; for example, the width may be as small as 0.1 nm or as great as tens of nanometers.

In the above exemplary implementations, each transmission structure's energy transmission function generally varies in a straight line direction, and each spreading component generally spreads light in the same straight line direction. It would be possible, however, to have a transmission function and spreading that occur in different, non-perpendicular directions and in directions that are not straight but rather are curved or angled.

Some of the above exemplary implementations involve specific materials, such as in photosensor arrays or position sensors and transmission structures, but the invention could be implemented with a wide variety of materials and with layered structures with various combinations of sublayers. In particular, photosensor arrays for a desired speed, sensitivity and wavelength range could have any suitable material, such as silicon, germanium, indium-gallium-arsenide, gallium arsenide, gallium nitride, or lead sulphide, and could be produced with any appropriate kind of devices, including, for example, photodiodes, avalanche photodiodes, p-i-n diodes, photoconductors, and so forth, with any appropriate technique for sensing and reading out information whether based on CCD, CMOS, or other techniques. Various commercially available detector arrays have pixel densities as high as ten megapixels, and some high density ICs have become relatively inexpensive.

Similarly, transmission structures could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in transmission structures may vary from 30 nm up to a few hundred nanometers.

Some of the above exemplary implementations involve particular types of transmission structures, such as Bragg mirrors and paired distributed Bragg reflectors separated by a Fabry-Perot cavity, but these transmission structures are merely exemplary, and any transmission structure that has laterally varying optical thickness could be used. Various techniques could be used to produce transmission structures with lateral variation in addition to those described above, including, during deposition, tilting the substrate, using a shadow mask, or using a temperature gradient to obtain graded layer thickness; also, during homogeneous deposition, off-axis doping, such as by e-beam, MBE, or MOVPE, could produce lateral variation.

Some of the above exemplary implementations employ enhanced light-target interaction to obtain fluorescence. In general, however, the techniques described above could also be used for light from self-emitting or auto-fluorescing objects such as particles. Furthermore, various types of fluorescence, photo-luminescence, chemo-fluorescence, inelastic scattering, and so forth could be employed. The technique of anti-resonant waveguiding, described above, is only one of many techniques that could be used for enhanced light-target interaction, and any such excitation technique could be applied continuously or intermittently along a path. Various parameters could be adjusted to obtain anti-resonant waveguiding, including the shape of quartz or glass surrounding the channel; a thinner structure is generally better, with a surface parallel to the channel generally being required.

Additional description of excitation techniques is found in co-pending U.S. patent application Ser. No. 11/316,660, entitled "Providing Light to Channels or Portions" and incorporated herein by reference in its entirety.

Some of the above exemplary implementations use specific stimulus-wavelength converters or other optical sensors or specific propagation components to obtain light with desired characteristics, but various other converting or sensing techniques and propagation components could be used within the scope of the invention. More specifically, some of the exemplary implementations include spreading components or separation components of specific types, but various other spreading components or separation components could be used within the scope of the invention. Some of the exemplary implementations show a specific number of aligned light sources, but the techniques could be used with any suitable number of light sources, and the light sources could be arranged in any appropriate way.

The exemplary implementation in FIG. 29 employs a CPU, which could be a microprocessor or any other appropriate component. Furthermore, as noted above, the adjustment of photosensed quantities could be done either digitally or with analog signals, and could be done either on the same IC as the photosensor array, on other components, or on a combination of the two, with any appropriate combination of software or hardware.

The above exemplary implementations generally involve production and use of ICs, transmission structures, stimulus-wavelength conversion techniques, propagation components, spreading components, separating components, and readout and comparing circuitry following particular operations, but different operations could be performed, the order of the operations could be modified, and additional operations could be added within the scope of the invention. For example, in implementations in which a transmission structure is on a separate substrate from a photosensor array, the transmission structure could be moved relative to the photosensor array between consecutive sensing operations. Also, readout of adjusted or unadjusted sensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. Apparatus comprising:
    a stimulus-wavelength converter that provides output light in response to one or more stimuli;
    a transmission structure that has an entry surface at which it receives the output light from the converter and an exit surface; the entry surface extending in a first direction in which the transmission structure has a laterally varying energy transmission function; and
    a spreading component that spreads the output light from the converter across the transmission structure's entry surface in at least a spreading direction that is not perpendicular to the first direction.

2. The apparatus of claim 1 in which the converter provides the output light within a range of photon energies; in response to spreaded output light received at the entry surface with energies in a given subrange of the range of energies, the transmission structure providing output photons at a respective position of the exit surface.

3. The apparatus of claim 1 in which the spreading direction is approximately the same as the first direction.

4. The apparatus of claim 1 in which the stimulus-wavelength converter includes a set of one or more optical fibers that each respond to a respective stimulus and provide output light to the spreading component.

5. The apparatus of claim 4 in which at least one of the set of optical fibers provides light output through an end positioned in a butting relationship adjacent the entry surface of the transmission structure; the spreading component including a surface at the end.

6. The apparatus of claim 4 in which at least one of the set of optical fibers provides light output through an end; the spreading component being positioned between the end and the entry surface of the transmission structure.

7. The apparatus of claim 6 in which the end and the entry surface are separated by a gap; the spreading component including at least one of air, gas, a transparent medium, or vacuum in the gap.

8. The apparatus of claim 6 in which the spreading component includes at least part of a lens between the end and the entry surface.

9. The apparatus of claim 8 in which the lens is a Selfoc® or gradient index lens.

10. The apparatus of claim 4 in which the set of optical fibers includes two or more optical fibers, each having an end through which it provides respective light output; the system further comprising:
    a separation component that keeps light output from the optical fibers separate.

11. The apparatus of claim 10 in which the separation component includes blades or includes at least one lens that collimates, images, or focuses.

12. The apparatus of claim 11 in which the separation component includes a positive anamorphic lens or lens group or includes a focusing lens and a negative anamorphic lens or lens group between the focusing lens and the entry surface of the transmission structure.

13. The apparatus of claim 12 in which the focusing lens is a Selfoc® or gradient index lens.

14. The apparatus of claim 10 in which the ends of the optical fibers are aligned in a second direction approximately perpendicular to the first direction; the spreading direction being approximately the same as the first direction.

15. The apparatus of claim 1 in which the stimulus-wavelength converter provides output light from a fiber end facet, from a point-like source, or from a broad area source.

16. The apparatus of claim 1, further comprising:
    one or more photosensing components that photosense output photons from the transmission structure's exit surface at a set of positions along the first direction.

17. The apparatus of claim 16 in which the photosensing components include at least one of a photosensor array, a position sensor, and a position sensor array.

18. A system that includes the apparatus of claim 16; the output light from the converter including wavelength information; the system further comprising:
    circuitry that responds to the photosensing components, providing signals indicating the wavelength information.

19. The system of claim 18 in which the circuitry includes a processor.

20. A sensing method comprising:
    receiving output light from a stimulus-wavelength converter, the converter providing the output light in response to one or more stimuli;
    spreading the output light received from the converter in at least a spreading direction across a transmission structure's entry surface;
    in response to the light spreaded across the entry surface, providing output photons at an exit surface of the transmission structure in accordance with an energy transmission function that varies laterally in a first direction in which the entry surface extends, the first direction and the spreading direction not being perpendicular to each other.

21. The method of claim 20 in which the output light from the stimulus-wavelength converter is provided through a set of optical fiber ends; the act of spreading the output light comprising at least one of:
propagating the output light through surfaces at the optical fiber ends;
propagating the output light through at least one of air, gas, a transparent medium, or vacuum; and
propagating the output light through a lens.

22. The method of claim 20, further comprising:
with one or more photosensing components, photosensing the output photons from the exit surface at a set of positions along the first direction.

23. The method of claim 22 in which the output light from the converter includes wavelength information, the method further comprising:
in response to photosensing results from the photosensor components, providing signals indicating the wavelength information.

24. Apparatus comprising:
two or more sources that provide light that includes wavelength information;
a transmission structure that has an entry surface at which it receives light and an exit surface, the entry surface extending in a first direction in which the transmission structure has a laterally varying energy transmission function; and
a propagation component that spreads the light from each source across the transmission structure's entry surface and keeps the light from the sources separate; the propagation component spreading the light in at least a spreading direction that is not perpendicular to the first direction.

25. The apparatus of claim 24 in which the light sources are aligned in a second direction approximately perpendicular to the first direction; the spreading direction being approximately the same as the first direction.

26. The apparatus of claim 24, further comprising:
one or more stimulus-wavelength converters that provide output light through the sources.

27. The apparatus of claim 24 in which each of the light sources is a fiber end facet, a point-like source, or a broad area source.

28. The apparatus of claim 24 in which each of the light sources is an optical fiber end positioned in a butting relationship adjacent the entry surface of the transmission structure; the propagation component including an optical fiber surface at each end.

29. The apparatus of claim 24 in which the propagation component is positioned between the sources and the entry surface of the transmission structure.

30. The apparatus of claim 29 in which the sources and the entry surface are separated by a gap; the propagation component including at least one of:
air, gas, a transparent medium, or vacuum in the gap;
one or more lenses; and
a set of blades.

31. The apparatus of claim 30 in which the propagation component includes at least one lens that collimates, images, or focuses.

32. The apparatus of claim 31 in which the separation component includes a positive anamorphic lens or lens group or includes a focusing lens and a negative anamorphic lens or lens group between the focusing lens and the entry surface of the transmission structure.

* * * * *